US012708607B2

(12) United States Patent
Kinsella et al.

(10) Patent No.: US 12,708,607 B2
(45) Date of Patent: Aug. 18, 2026

(54) THROMBOXANE RECEPTOR ANTAGONIST FORMULATIONS

(71) Applicant: ATXA THERAPEUTICS LIMITED, Dublin (IE)

(72) Inventors: B. Therese Kinsella, Dublin (IE); Helen Reid, Dublin (IE); Eamon Mulvaney, Dublin (IE)

(73) Assignee: ATXA THERAPEUTICS LIMITED, Dublin (IE)

( * ) Notice: Subject to any disclaimer, the term of this patent is extended or adjusted under 35 U.S.C. 154(b) by 597 days.

(21) Appl. No.: 18/014,438

(22) PCT Filed: Jul. 6, 2021

(86) PCT No.: PCT/EP2021/068672

§ 371 (c)(1),
(2) Date: Jan. 4, 2023

(87) PCT Pub. No.: WO2022/008515

PCT Pub. Date: Jan. 13, 2022

(65) Prior Publication Data

US 2023/0301946 A1 Sep. 28, 2023

Related U.S. Application Data

(60) Provisional application No. 63/048,856, filed on Jul. 7, 2020.

(51) Int. Cl.
*A61K 31/18* (2006.01)
*A61K 9/16* (2006.01)

(52) U.S. Cl.
CPC ............ *A61K 31/18* (2013.01); *A61K 9/1635* (2013.01)

(58) Field of Classification Search
CPC .............................. A61K 31/18; A61K 9/1635
See application file for complete search history.

(56) References Cited

U.S. PATENT DOCUMENTS 4,256,108 A 3/1981 Theeuwes
4,265,874 A 5/1981 Bonsen et al.
5,319,041 A * 6/1994 Zhong .................. C08F 226/10 526/330
6,214,841 B1 4/2001 Jackson et al.
6,706,283 B1 * 3/2004 Appel .................. A61K 9/0004 424/464
9,388,127 B2 7/2016 Kinsella et al.
9,522,877 B2 12/2016 Kinsella et al.
9,630,915 B2 4/2017 Kinsella et al.
9,718,781 B2 8/2017 Kinsella et al.
9,738,599 B2 8/2017 Kinsella et al.
9,932,304 B2 4/2018 Kinsella et al.
10,357,504 B2 7/2019 Kinsella et al.
10,966,994 B2 4/2021 Kinsella et al.
2003/0232877 A1 12/2003 Sikorski et al.
2010/0151035 A1 * 6/2010 Ramaswami ........ A61K 31/397 514/288
2011/0014282 A1 * 1/2011 de Vasconcelos ...... A61P 43/00 424/452
2016/0120809 A1 * 5/2016 Djordjevic ........... A61K 9/2027 514/249
2018/0179152 A1 * 6/2018 Kinsella .................. A61P 35/00

FOREIGN PATENT DOCUMENTS

KR 20050045630 5/2005
WO 2005004917 1/2005
WO 2013156861 10/2013
WO 2013156871 10/2013
WO 2016203314 12/2016

OTHER PUBLICATIONS

Sun et al., "Probing the mechanisms of drug release from amorphous solid dispersions in medium-soluble and medium-insoluble carriers," Journal of Controlled Release, vol. 211, Aug. 10, 2015, pp. 85-93. (Year: 2011).*
Francesco Tres et al., "Indomethacin-Kollidon VA64 Extrudates: A Mechanistic Study of pH-Dependent Controlled Release", Molec Pharma, (13):1166-1175.
Li Jing-yuan et al., "The impact of glimepiride precipitation inhibitors on their solid dispersions", J of Shenyang Pharma Univ, (34)6:451-460.
Buhler, "Kollidon: Polyvinylpyrrolidone excipients for the pharmaceutical industry", BASF SE Pharma Ingredients & Services, 2009.
Chang, et al., "Polymethacrylates, monograph", Handbook of Pharmaceutical Excipients, 6Ed, Rowe et al., Eds., Pharmaceutical Press (London, UK), 2009, 525-533.

(Continued)

*Primary Examiner* — Jared Barsky
(74) *Attorney, Agent, or Firm* — Zachary D. Hyde; Sullivan & Worcester LLP

(57) ABSTRACT

The present invention provides formulations that enhances bioavailability of thromboxane receptor antagonists allowing them to bind to the thromboxane $A_2$ receptors in subjects suffering from disease indications in which the prostanoid thromboxane $A_2$, and incidental thromboxane $A_2$ receptor ligands, are implicated. The formulations comprise a solid dispersion comprising a benzenesulfonyl urea and a polymer that are suitable for administration through oral or other routes of delivery.

9 Claims, 18 Drawing Sheets

(56) References Cited

OTHER PUBLICATIONS

Mulvaney, et al., BMC Pulmonary Medicine, 2020, 20:85.
Mulvaney, et al., Eur J Pharmacol, 2020, 889:173658.
BASF, 2025, 'Technical Information: Kollidon VA 64, Kollidon VA 64 Fine', BASF Pharma Solutions, Florham Park, NJ, 07932 (16 pages).
CDER, 1997, 'Guidance for Industry: Dissolution Testing of Immediate Release Solid Oral Dosage Forms', U.S. Department of Health and Human Services, Food and Drug Administration, Center for Drug Evaluation and Research (CDER), Rockville, MD (17 pages).

* cited by examiner

| Pharmacokinetic Parameter | IV Control (1 mg/kg)[1] | *NTP42*:KVA4[2] 25 mg/kg (5 mg/kg API) | | |
|---|---|---|---|---|
| | | (i) 0.5 % HMPC E3 | (ii) Gelatin Capsules | (iii) HPMC Capsules |
| $C_{max}$ (ng/ml; μM) | 8,140 (15.8 μM) | 21,000 (40.7 μM) | 19,800 (38.4 μM) | 20,900 (40.5 μM) |
| $T_{max}$ (min) | 17.3 | 25 | 120 | 165 |
| Elimination $T_{1/2}$ (hr) | 6.37 | 7.35 | 7.53 | 15 |
| $AUC_{0-t}$ (ng·hr/ml) | 35,333 | 128,167 | 155,833 | 139,000 |
| $AUC_{0-\infty}$ (ng·hr/ml) | 38,333 | 142,333 | 176,667 | 181,667 |
| Bioavailability (F%, $AUC_{0-t}$) | - | 72.5 | 88.2 | 78.7 |
| Bioavailability (F%, $AUC_{0-\infty}$) | - | 74.3 | 92.2 | 94.8 |

1 *NTP42* was administered by IV (1 mg/kg) in a dosing vehicle composed of DMSO, Cremophor-EL and PBS (10 %: 10 %: 80 % v/v/v ratio).

2 For the assessments of SDD formulations as 'Drug-in-Bottle' and 'Drug-in-Capsule' formats in *in vivo* rat pharmacokinetic (PK) studies, spray-dried material was filled into (ii) gelatin and (iii) HPMC capsules for the 'Drug-in-Capsule' format and was compared to 'Drug-in-Bottle' format, where SDD material was administered as a suspension in 0.5 % HPMC-E3 (w/v) dosing vehicle. Note that rats were fasted 16 hr prior to administration of drug. Data presented are the mean values from 4 independent animals from each administration group.

FIG. 6

| Pharmacokinetic Parameter | IV Control (1 mg/kg)[1] | ***NTP42***:Kollidon® VA 64 (1:4)[2] | ***NTP42***: Kollidon® VA 64 (1:8)[2] |
|---|---|---|---|
| **$C_{max}$ (ng/ml; µM)** | 11,800 (22.9 µM) | 14,200 (27.5 µM) | 13,400 (26 µM) |
| **$T_{max}$ (min)** | 19 | 32.5 | 25 |
| **Elimination $T_{1/2}$ (hr)** | 5.87 | 5.78 | 7.98 |
| **$AUC_{0-t}$ (ng·hr/ml)** | 48,833 | 79,000 | 86,333 |
| **$AUC_{0-\infty}$ (ng·hr/ml)** | 51,667 | 83,167 | 97,667 |
| **Bioavailability (F%, $AUC_{0-t}$)** | - | 32.7 | 35.7 |
| **Bioavailability (F%, $AUC_{0-\infty}$)** | - | 32.2 | 37.8 |

[1] *NTP42* was administered by IV (1 mg/kg) in a dosing vehicle composed of DMSO, Cremophor-EL and PBS (10 %: 10 %: 80 % v/v/v ratio).
[2] For the assessment of SDD formulations as 'Drug-in-Bottle' format in *in vivo* rat pharmacokinetic (PK) studies, spray-dried material was administered in dosing vehicle, 0.5 % HPMC-E3.

FIG. 14

| Drug Treatment Group | No MCT Control | MCT Only Placebo | NTP42:KVA4 1 mg/kg BID |
|---|---|---|---|
| Mean Pulmonary Arterial Pressure mPAP (mmHg) | 13.9 ± 0.84 (6) | 40.5 ± 3.90 (11) | 27.6 ± 3.65 (8) |
| Right Ventricular Systolic Pressure RVSP (mmHg) | 19.9 ± 0.76 (5) | 66.7 ± 6.72 (11) | 37.8 ± 3.27 (7) |
| Mean Systemic Arterial Pressure mAP (mmHg) | 103.7 ± 10.42 (6) | 91.9 ± 3.30 (11) | 99.8 ± 7.10 (8) |
| Heart Rate HR (bpm) | 308 ± 28 (6) | 305 ± 4 (11) | 311 ± 15 (8) |
| Pulmonary Vascular Remodelling Vessel Occlusion (%) | 20.0 ± 0.73 (6) | 33.4 ± 1.47 (11) | 26.6 ± 1.28 (7) |
| Pulmonary Vascular Remodelling Fully-muscularised (α-SMA) Vessels (%) | 4.3 ± 1.61 (6) | 29.7 ± 3.07 (11) | 14.2 ± 2.77 (8) |
| Right Ventricular Hypertrophy Fulton's Index | 0.280 ± 0.004 (5) | 0.594 ± 0.018 (9) | 0.442 ± 0.039 (8) |
| Right Ventricular Fibrosis (% Area) | 4.6 ± 0.03 (5) | 12.4 ± 1.19 (11) | 6.6 ± 0.46 (7) |
| Pulmonary Fibrosis Fibrosis/Vessel Thickness Ratio | 0.07 ± 0.00 (4) | 0.16 ± 0.02 (11) | 0.10 ± 0.01 (7) |
| Pulmonary Inflammation Macrophages ($CD68^+$ Cells/$mm^2$) | 78.0 ± 4.56 (5) | 493.3 ± 28.52 (11) | 112.3 ± 15.21 (8) |

FIG. 26

THROMBOXANE RECEPTOR ANTAGONIST FORMULATIONS

TECHNICAL FIELD

The disclosure relates to oral delivery formulations of thromboxane receptor antagonists.

BACKGROUND

Individuals suffering from imbalances in the levels of the T prostanoid thromboxane $A_2$, or imbalances in signaling of its receptor, may suffer from disorders that interfere with multiple vital systems of the body, including the cardiovascular, renal, pulmonary, and prostate systems. More recently, T prostanoid thromboxane $A_2$, T prostanoid thromboxane $A_2$ synthase, and the T prostanoid receptor have also been implicated in neoplastic disease conditions, including in cancers of the bladder, prostate, breast and lung where T prostanoid thromboxane $A_2$ can promote tumor cell proliferation, migration, invasion, angiogenesis, inflammation and immunity, amongst other tumor-promoting actions.

Despite knowledge of the role of the T prostanoid thromboxane $A_2$ and its receptor, many individuals continue to suffer from these imbalances and their devastating effects without receiving appropriate treatment. Traditional therapeutic approaches aim to inhibit the biosynthesis of T prostanoid thromboxane $A_2$. Amongst these are the class of cyclooxygenase inhibitors referred to as the non-steroidal anti-inflammatory drugs, which includes Aspirin and related cyclooxygenase 1 and/or cyclooxygenase 2 inhibitors. Low-dose Aspirin remains widely used to prevent excessive thrombosis in patients at risk of cardiovascular episodes by inhibiting T prostanoid thromboxane $A_2$ generation.

Approaches involving the use of low-dose Aspirin, however, are not sufficiently effective and cause associated side-effects due to their indiscriminate inhibition of the synthesis of the other prostanoids (prostaglandin $D_2$, prostaglandin $E_2$, prostaglandin $F_{2\alpha}$ and prostaglandin $I_2$/prostacyclin). Lack of efficacy can also occur because a relatively high percentage of the general population displays aspirin-resistance, contributing to the general failure to lower T prostanoid thromboxane $A_2$ levels in response to Aspirin therapy. Furthermore, increased incidence of adverse cardiovascular episodes can occur in patients receiving cyclooxygenase IB (cyclooxygenase 2 selective inhibitors) therapy.

As a result, many individuals with T prostanoid thromboxane $A_2$ imbalances continue to suffer without receiving an effective treatment or from the side-effects of only partially-effective treatments.

SUMMARY

The disclosure provides a formulation of a thromboxane $A_2$ receptor antagonist drug with a vinylpyrrolidone-vinyl acetate copolymer for oral dosing for human use. The drug is protected in the low pH of the stomach, remaining intact as a drug:polymer complex, but ready for dissolution at the higher pH of the intestine for maximal absorption. The present invention provides formulations that allow the thromboxane receptor antagonist to bind prostanoid thromboxane $A_2$ receptors in subjects suffering from a prostanoid thromboxane $A_2$ imbalance in order to effectively balance prostanoid thromboxane levels. The formulations comprise a solid dispersion comprising the thromboxane receptor antagonist and a pharmaceutically acceptable polymer that are suitable for oral administration. Once formulations of the invention are administered, cardiovascular, renal, pulmonary, and prostate systems can be rescued from dysfunction and eventual collapse. Moreover, risk and proliferation of cancers of the bladder, prostate, breast and lung from T prostanoid thromboxane $A_2$ related-disorders can be prevented.

Substituted benzenesulfonyl urea compounds of formulations of the invention can bind to thromboxane $A_2$ receptors and inhibit thrombosis and other events within the cardiovascular, renal, pulmonary, or other systems where the thromboxane $A_2$ receptor is expressed including, but not limited to, platelets, various types of smooth muscle cells, endothelial cells, monocytes/macrophages, keratinocytes, primary afferent neurons and certain cells of the immune system.

Substituted benzenesulfonyl urea compounds have good permeability but may have poor solubility. This can significantly lower their bioavailability, particularly in oral formulations. Advantageously, formulations of the invention provide a significant solubility enhancement for a drug comprising a substituted benzenesulfonyl urea, maximizing their absorption and oral bioavailability. As a result, the formulations are protected from the acidic environment of the stomach, with a pH of ~1.6 but disperse in higher pH environments of the intestine, with a pH of ~6.5 where it may maximally absorbed. Formulations of the invention may provide a suitable oral dose form. Formulations of the present invention may allow a drug comprising a substituted benzenesulfonyl urea with relatively poor solubility, with the solubility enhancement to maximize its absorption, oral bioavailability, and exposure.

Formulation of the invention may be more insoluble in lower pH environments than in higher pH environments. For example, formulations of the invention may be substantially insoluble at a pH of less than 2. Formulation of the invention may be substantially soluble at a pH above 5.

Formulations of the invention may have the added advantage over other pulmonary arterial hypertension therapeutic agents used in that such compounds would not only inhibit T prostanoid thromboxane $A_2$, the main vaso-constricting prostaglandin produced in the lung but also inhibit the adverse actions of the oxidative-stress derived isoprostane 8-iso-prostaglandin $F_{2\alpha}$, in addition to those of T prostanoid thromboxane $A_2$ itself. Besides pulmonary arterial hypertension, in other diseases such as atherothrombosis replacing the standard-of-care Aspirin with formulations of the invention offer several advantages as they may: (i) not only block the action of T prostanoid thromboxane $A_2$, prostaglandin $G_2$/prostaglandin $H_2$ and 20-Hydroxyeicosatetraenoic acid, but also of Aspirin-insensitive thromboxane $A_2$ receptor agonists (e.g., 8-iso-prostaglandin $F_{2\alpha}$, generated in abundance by free-radicals during oxidative injury); (ii) also (unlike Aspirin), will inhibit the thromboxane $A_2$ receptor expressed in cells of the vascular bed and in circulating macrophages/monocytes, present during the inflammatory atherothrombosis; (iii) overcome Aspirin-resistance, estimated to occur in ~33% of the population.

The polymer of formulations of the invention may be a vinylpyrrolidone-vinyl acetate copolymer. The vinylpyrrolidone-vinyl acetate copolymer may be a vinylpyrrolidone-vinyl acetate copolymer as sold under the trademark KOLLIDON VA64 by BASF SE (Ludwigshafen, Germany). The polymer of formulations of the invention may be a dimethylaminoethyl methacrylate-copolymer such as the dimethylaminoethyl methacrylate-copolymer sold under the trademark EUDRAGIT EPO by Evonik Industries AG (Essen, Germany).

The polymer of formulations of the invention may be a methacrylic acid and methyl methacrylate anionic copolymer. The methacrylic acid and methyl methacrylate copolymer may be as sold under the trademark EUDRAGIT L100 by Evonik Industries AG (Essen, Germany).

The polymer of formulations of the invention may be the polymer hydroxypropyl methylcellulose or hydroxypropyl methylcellulose acetate succinate.

The polymer of formulations of the invention may be combined with plasticizers, for example, a solubilizer and emulsifying agent such as polyoxyl 40 hydrogenated castor oil or macrogolglycerol hydroxystearate sold under the trademark KOLLIPHOR RH40 by BASF.

Formulations of the invention may be amorphous solid dispersions. Formulations of the invention may be spray dried dispersions. Advantageously, the formulation may be formulated in an oral dose form.

An advantage of the formulation approach of the present invention, for example, spray solid dispersions formulations, is that the vinylpyrrolidone-vinyl acetate copolymer may confer a protection to the benzenesulfonyl urea, shielding it from the low pH of the stomach (for example, as can be simulated through drug dissolution studies in Fasted State Simulated Gastric Fluid (FaSSGF) with a pH ~1.6), maintaining it in a benzenesulfonyl urea:vinylpyrrolidone-vinyl acetate copolymer complex until it is subsequently released on passage to the higher pH of the small intestine (for example, as simulated in Fasted State Simulated Intestinal Fluid (FaSSIF) with a pH ~6.5). Advantageously, the benzenesulfonyl urea in a benzenesulfonyl urea:vinylpyrrolidone-vinyl acetate copolymer spray solid dispersion formulation would be protected from the acidic environment of the stomach (~pH 1.6) and disperse in the higher pH environment of the intestine where it may be maximally absorbed.

Oral dose forms may further be in the form of a tablet, vial, sachet, or capsule.

The formulations may further comprise a ratio of the benzenesulfonyl urea to vinylpyrrolidone-vinyl acetate copolymer of between 1:1 and 1:8. For example, the formulation may comprise a ratio of benzenesulfonyl urea: vinylpyrrolidone-vinyl acetate copolymer of 1:4.

Advantageously, the formulations of the invention may be used in a method, or for use in treating a condition selected from the group consisting of: pulmonary arterial hypertension, other pulmonary and cardiopulmonary diseases, atherothrombosis, stroke, myocardial infarction, atherosclerosis, arteriosclerotic vascular disease, thromboembolism, deep vein thrombosis, arterial thrombosis, ischemia, peripheral vascular disease, peripheral artery occlusive disease, coronary artery disease, angina pectoris, kidney diseases, urology diseases and transient ischemic attack in a patient in need thereof, the method comprising administering to a patient the formulation of the invention.

Advantageously, the formulations of the invention may be used in a method, or for use in treating a proliferative disorder selected from the group consisting of, including but not limited to: non-Hodgkin's lymphoma, colorectal, esophageal, prostate, ovary, breast, pancreatic, bladder, colon, lung and ovarian cancer in a patient in need thereof, the method comprising administering to a patient the formulation of the invention.

Advantageously, the formulations of the invention may be used in a method, or for use in treating a viral infection, inflammatory or fibrotic conditions selected from the group consisting of pulmonary conditions including but not limited to: pneumonia, pulmonary hypertensions, pulmonary arterial hypertension, interstitial lung diseases, idiopathic pulmonary fibrosis, asthma, acute lung inflammation and chronic obstructive pulmonary disease (COPD) in a patient in need thereof, the method comprising administering to a patient the formulation of the invention.

In aspects of the invention, the drug comprising a substituted benzenesulfonyl urea used in formulations of the invention is a compound of formula (I):

(I)

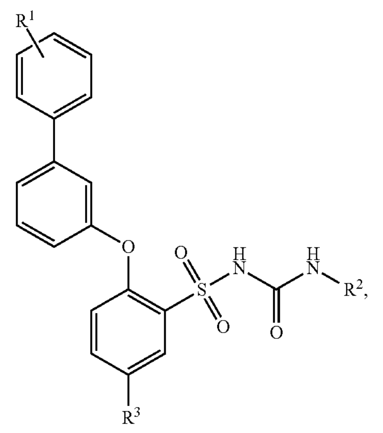

wherein $R^1$ is a cycloalkyl group, an alkyl group, a heterocycloalkyl group, a difluoromethyl group, a trifluoromethyl group, a halogenated cycloalkyl group, a halogenated alkyl group, a halogenated heterocycloalkyl group, a methoxy group, a halogenated methoxy group, an ethoxy group, an isopropoxy group, a tert-butoxy group, a halogenated ethoxy group, a halogenated isopropoxy group, a halogenated tert-butoxy group, a primary amide ($—CONH_2$), a secondary amide ($—CONHCH_3$), a tertiary amide ($—CONH(CH_3)_2$), or a nitrile group; $R^2$ is an alkyl group of 2 to 6 carbons, and a halogenated alkyl group of 2 to 6 carbons; and $R^3$ is a nitrile group or nitro group, or a pharmaceutically acceptable salt thereof. In a preferred embodiment, $R^3$ is a nitrile group.

In aspects of the invention, the benzenesulfonyl urea is a compound of formula (IV):

(IV)

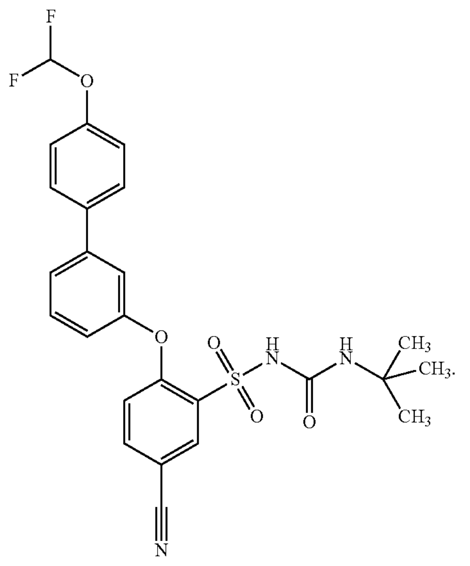

In an aspect of the invention, provided is a formulation comprising a compound of formula (IV):

(IV)

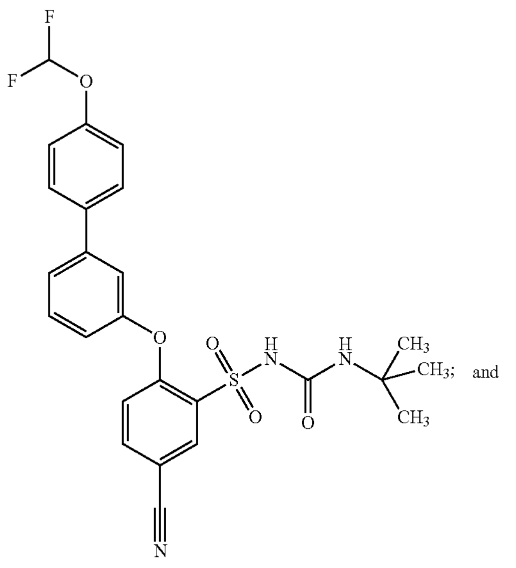

and a vinylpyrrolidone-vinyl acetate in a ratio of 1:4 compound of formula (IV): vinylpyrrolidone-vinyl acetate copolymer, wherein the formulation is substantially insoluble at a pH of less than 2 and is substantially soluble at a pH above 5.

The formulation may be a spray dried dispersion.

The formulation may be further formulated as an oral dose form. The oral dose form may be in the form of a tablet, vial, sachet, or capsule.

Advantageously, the formulations of the invention may be used in a method, or for use in treating a condition selected from the group consisting of: pulmonary arterial hypertension, other pulmonary and cardiopulmonary diseases, atherothrombosis, stroke, myocardial infarction, atherosclerosis, arteriosclerotic vascular disease, thromboembolism, deep vein thrombosis, arterial thrombosis, ischemia, peripheral vascular disease, peripheral artery occlusive disease, coronary artery disease, angina pectoris, kidney diseases, urology diseases, and transient ischemic attack in a patient in need thereof, the method comprising administering to a patient the formulation of the invention.

Advantageously, the formulations of the invention may be used in a method, or for use in treating a proliferative disorder selected from the group consisting of: non-Hodgkin's lymphoma, colorectal, esophageal, prostate, ovary, breast, pancreatic, bladder, colon, lung and ovarian cancer in a patient in need thereof, the method comprising administering to a patient the formulation of the invention.

Advantageously, the formulations of the invention may be used in a method, or for use in treating a viral infection, inflammatory or fibrotic condition selected from the group consisting of pulmonary conditions including but not limited to: pneumonia, pulmonary hypertensions, pulmonary arterial hypertension, interstitial lung diseases, idiopathic pulmonary fibrosis, asthma, acute lung inflammation and chronic obstructive pulmonary disease (COPD) in a patient in need thereof, the method comprising administering to a patient the formulation of the invention.

BRIEF DESCRIPTION OF THE DRAWINGS

FIG. 6 shows a table of pharmacokinetic data for a formulation of the present invention.

FIG. 14 shows a table of pharmacokinetic data for formulations of the present invention.

FIG. 26 is a table showing the effect of NTP42:KVA4 on MCT PAH in rats.

DETAILED DESCRIPTION

Figure 1:
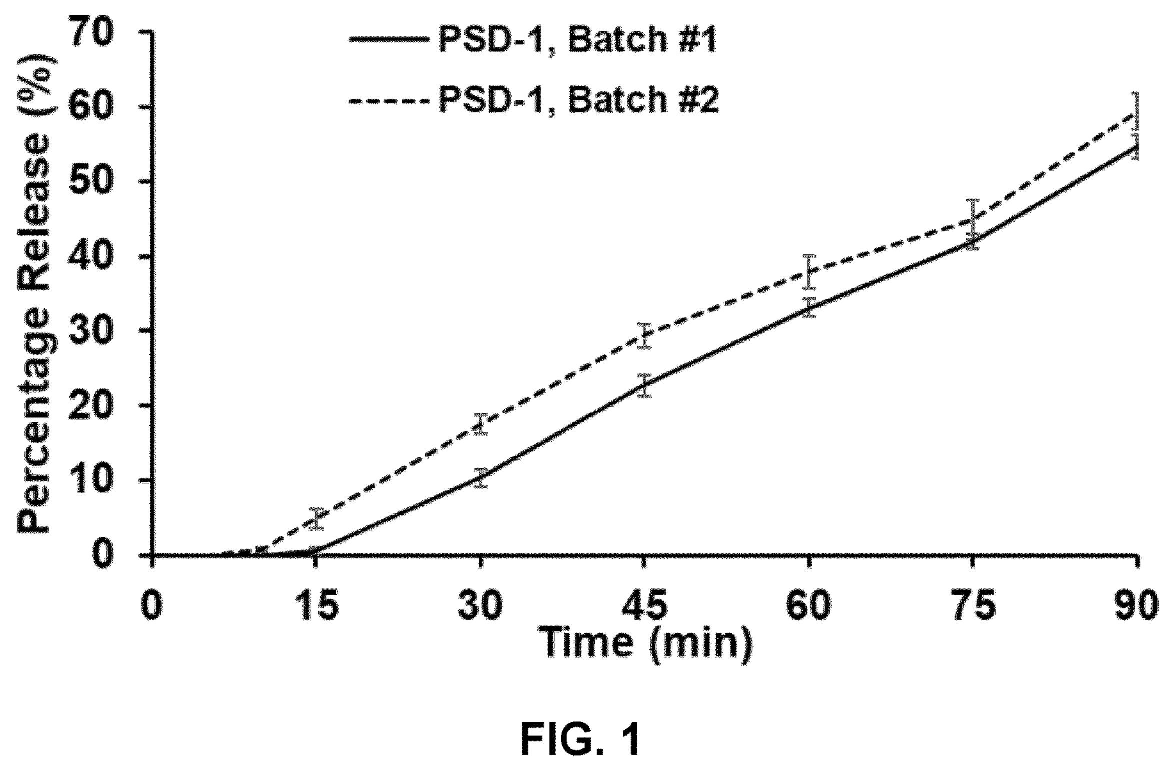
FIG. 1 shows a graph of the release rate of a formulation of the present invention.

The present invention provides formulations comprising a benzenesulfonyl urea and a polymer that enables bioavailability of the benzenesulfonyl urea to allow it bind prostanoid thromboxane $A_2$ receptors in subjects suffering from disease indications in which the prostanoid thromboxane $A_2$, and incidental thromboxane $A_2$ receptor ligands listed below, are implicated. The formulations comprise a solid dispersion comprising a benzenesulfonyl urea and a polymer (e.g., vinylpyrrolidone-vinyl acetate) that are suitable for oral administration. Benzenesulfonyl urea is an antagonist of T prostanoid thromboxane $A_2$, and other incidental thromboxane $A_2$ receptor ligands including the endoperoxide prostaglandin $G_2/H_2$, 20-Hydroxyeicosatetraenoic acid and isoprostanes (e.g., 8-iso-prostaglandin $F_{2\alpha}$) binding to the thromboxane $A_2$ receptor and stimulating platelet activation and aggregation, thereby decreasing the risk of a clinically significant thrombus or embolus, or antagonize the thromboxane $A_2$ receptor $\alpha$ and/or thromboxane $A_2$ receptor $\beta$ isoforms expressed in cells of the cardiovascular, renal, pulmonary or other systems, such as but not limited to conditions of the skin. Thus, the formulations of the invention provide beneficial pharmaceutical properties for treating thrombosis, inflammation, fibrosis, cell proliferation, blood vessel remodelling and other events within the cardiovascular, renal, pulmonary, pruritus (itch), dermatitis or other systems where the thromboxane $A_2$ receptor is expressed and/or where its ligands are dysregulated.

The drug comprising a substituted benzenesulfonyl urea used in formulations of the invention may be a compound of formula (I):

(I)

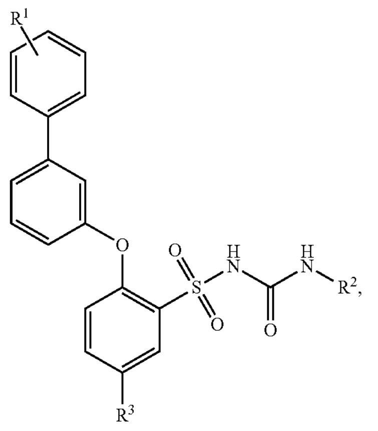

wherein $R^1$ is a cycloalkyl group, an alkyl group, an aryl group, a heterocycloalkyl group, a difluoromethyl group, a trifluoromethyl group, a halogenated cycloalkyl group, a halogenated alkyl group, a halogenated aryl group, a halogenated heterocycloalkyl group, a methoxy group, a halogenated methoxy group, an ethoxy group, an isopropoxy group, a tert-butoxy group, a halogenated ethoxy group, a halogenated isopropoxy group, a halogenated tert-butoxy group, a primary amide (—$CONH_2$), a secondary amide (—$CONHCH_3$), a tertiary amide (—$CONH(CH_3)_2$), or a nitrile group; $R^2$ is an alkyl group of 2 to 6 carbons, and a halogenated alkyl group of 2 to 6 carbons; and $R^3$ is a nitrile group or nitro group, or a pharmaceutically acceptable salt thereof. In a preferred embodiment, $R^3$ is a nitrile group.

The formulation of the invention may comprise a benzenesulfonyl urea in wherein $R^2$ is a tert butyl group, $R^3$ is a nitrile group; and $R^1$ is a cycloalkyl group, an alkyl group, an aryl group, a heterocycloalkyl group, a difluoromethyl group, a trifluoromethyl group, a halogenated cycloalkyl group, a halogenated alkyl group, a halogenated aryl group, a halogenated heterocycloalkyl group, a methoxy group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, or a nitrile group.

In aspects of the invention, the substituted benzenesulfonyl urea is a compound of formula (IV):

(IV)

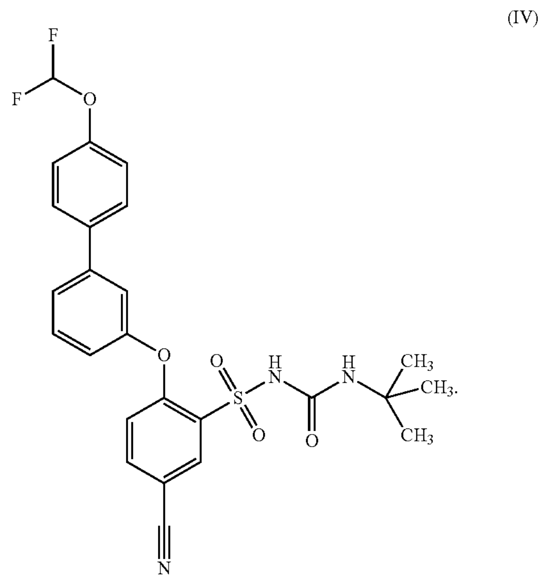 [SMILES: CC(C)(C)NC(=O)NS(=O)(=O)c1cc(C#N)ccc1Oc1cccc(-c2ccc(OC(F)F)cc2)c1]

Additional benzenesulfonyl urea may be used in formulations of the present invention.

The substituted benzenesulfonyl urea may be one or more of the compounds described below. For example, the benzenesulfonyl urea may be a compound represented by formula (I): where $R^1$ is selected from the group consisting of: a halogen, an alkyl group, a cycloalkyl group, an aryl group, a heterocycloalkyl group, a halogenated alkyl group, a halogenated cycloalkyl group, a halogenated aryl group, a halogenated heterocycloalkyl group, a methoxy group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, OH, a halogen, $CO_2H$, methyl ketone, a nitrile group, a methyl ester group, an ethyl ester group, an isopropyl ester group, a tert-butyl ester group, a halogenated methyl ester group, a halogenated ethyl ester group, a halogenated isopropyl ester group, and a halogenated tert-butyl ester group; and $R^2$ is selected from the group consisting of a halogen, an alkyl group, a halogenated alkyl group, an aryl group, and a halogenated aryl group, or a pharmaceutically acceptable salt thereof. In a preferred embodiment, $R^1$ is selected from the group consisting of: a halogen, an alkyl group, a halogenated alkyl group, a halogenated cycloalkyl group, a halogenated aryl group, a halogenated heterocycloalkyl group, a methoxy group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, and a nitrile group; and $R^2$ is selected from the group consisting of a halogen, an alkyl group, a halogenated alkyl group, an aryl group, and a halogenated aryl group, or a pharmaceutically acceptable salt thereof.

In certain embodiments, the invention provides a compound of formula (I), in which $R^1$ is selected from the group consisting of: a halogenated alkyl group, a halogenated methoxy group, a primary amide, a secondary amide, a tertiary amide, and a nitrile group; and $R^2$ is selected from the group consisting of an alkyl group of 3 to 6 carbons, and a halogenated alkyl group of 3 to 6 carbons, or a pharmaceutically acceptable salt thereof.

In certain embodiments, the invention provides a compound of formula (I), in which $R^1$ is selected from the group consisting of: a difluoromethyl group, a trifluoromethyl group, a difluormethoxy group, a trifluormethoxy group, a primary amide, a secondary amide, a tertiary amide, and a nitrile group; and $R^2$ is selected from the group consisting of an alkyl group of 6 or fewer carbons and a halogenated alkyl group of 6 or fewer carbons, or a pharmaceutically acceptable salt thereof.

In other embodiments, the invention provides a compound of formula (II):

(II)

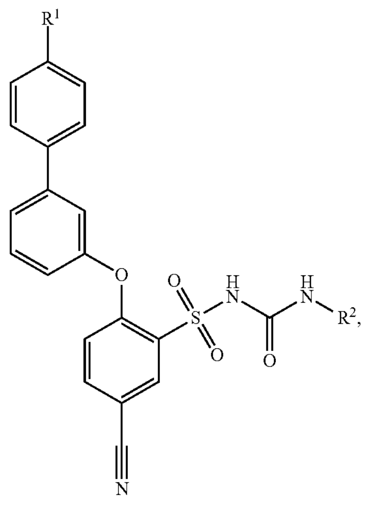

where $R^1$ is selected from the group consisting of: a halogen, an alkyl group, a cycloalkyl group, an aryl group, a heterocycloalkyl group, a halogenated alkyl group, a halogenated cycloalkyl group, a halogenated aryl group, a halogenated heterocycloalkyl group, a methoxy group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, OH, a halogen, $CO_2H$, methyl ketone, a nitrile group, a methyl ester group, an ethyl ester group, an isopropyl ester group, a tert-butyl ester group, a halogenated methyl ester group, a halogenated ethyl ester group, a halogenated isopropyl ester group, and a halogenated tert-butyl ester group; and $R^2$ is selected from the group consisting of a halogen, an alkyl group, a halogenated alkyl group, an aryl group, and a halogenated aryl group, or a pharmaceutically acceptable salt thereof.

In other embodiments, the invention provides a compound of formula (II), in which $R^1$ is selected from the group consisting of: a halogen, an alkyl group, a halogenated alkyl group, a halogenated cycloalkyl group, a halogenated aryl group, a halogenated heterocycloalkyl group, a methoxy group, a halogenated methoxy group, an ethoxy group, an isopropoxy group, a tert-butoxy group, a halogenated ethoxy group, a halogenated isopropoxy group, a halogenated tert-butoxy group, a primary amide, a secondary amide, a tertiary amide, and a nitrile group; and $R^2$ is selected from the group consisting of an alkyl group of 2 to 6 carbons, and a halogenated alkyl group of 2 to 6 carbons, or a pharmaceutically acceptable salt thereof.

In other embodiments, the invention provides a compound of formula (II), in which $R^1$ is selected from the group consisting of: a halogenated alkyl group, a halogenated methoxy group, a primary amide, a secondary amide, a tertiary amide, and a nitrile group; and $R^2$ is an alkyl group of 3 to 6 carbons, or a pharmaceutically acceptable salt thereof.

In a much preferred embodiment, the invention provides a compound of formula (II), in which $R^1$ is selected from the group consisting of: a difluoromethyl group, a trifluoromethyl group, a difluormethoxy group, a trifluormethoxy group, a primary amide, a secondary amide, a tertiary amide, and a nitrile group; and $R^2$ is selected from the group consisting of an alkyl group of 3 to 5 carbons and a halogenated alkyl group of 3 to 5 carbons, or a pharmaceutically acceptable salt thereof.

In embodiments, the invention provides a compound of formula (III):

(III)

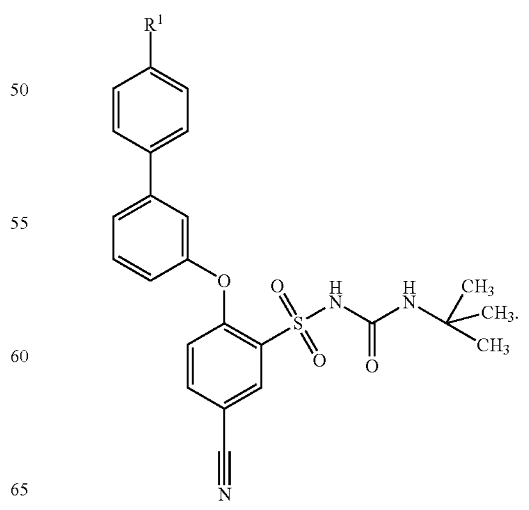

in which $R^1$ is selected from the group consisting of a difluoromethyl group, a trifluoromethyl group, a difluormethoxy group, a trifluormethoxy group, a primary amide, a secondary amide, a tertiary amide, and a nitrile group, or a pharmaceutically acceptable salt thereof. For example, the compound may be represented by formula (M), (V), (VI), (VII), (VI), (IX), (X), or (XI):

(IV)

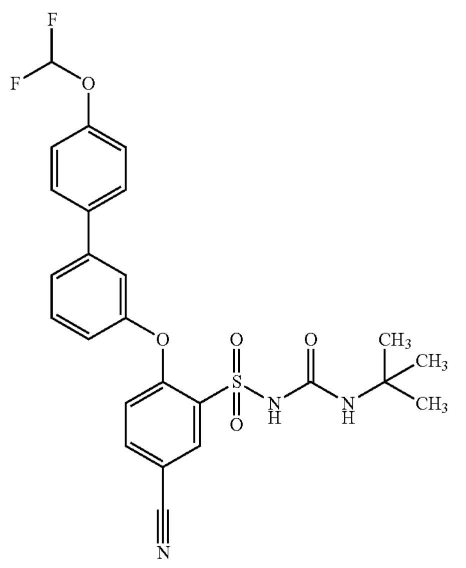

(V)

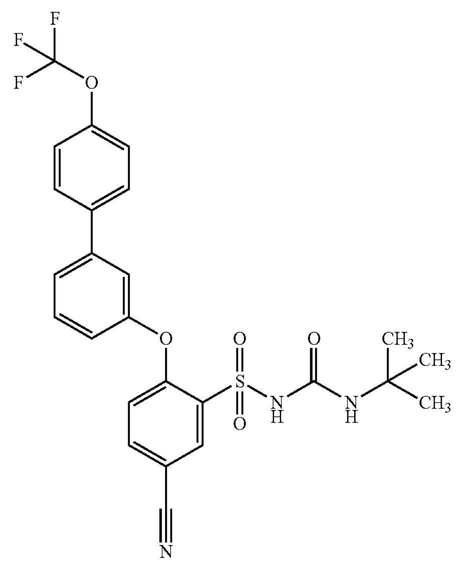

-continued (VI)

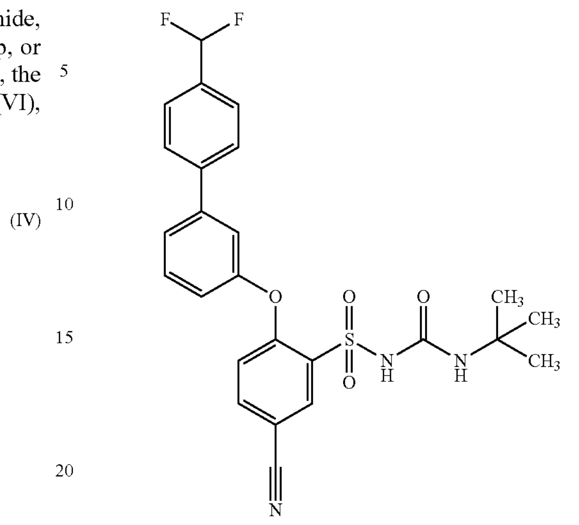

(VII)

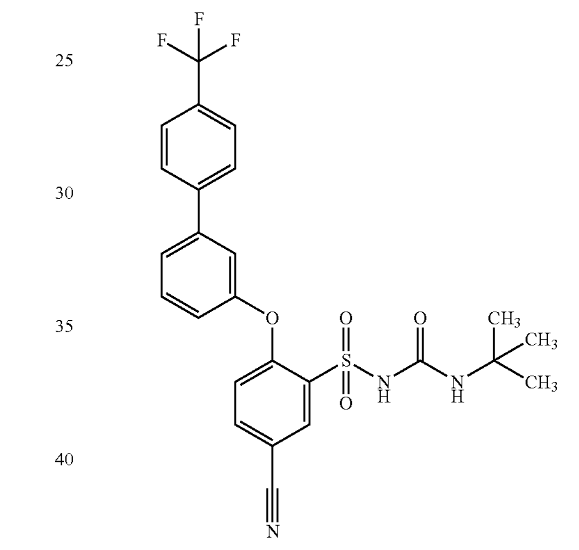

(VIII)

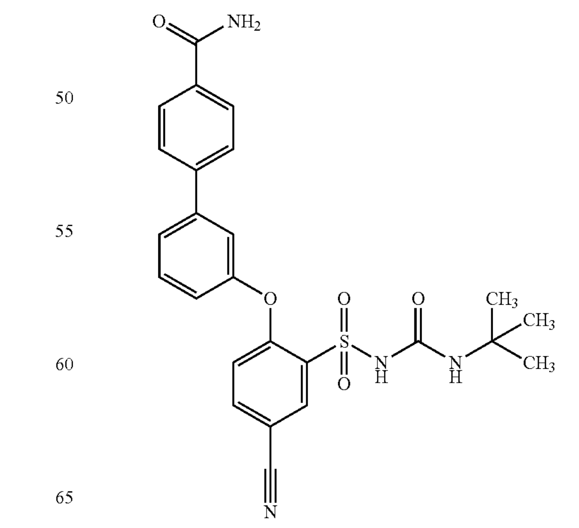

-continued (IX)

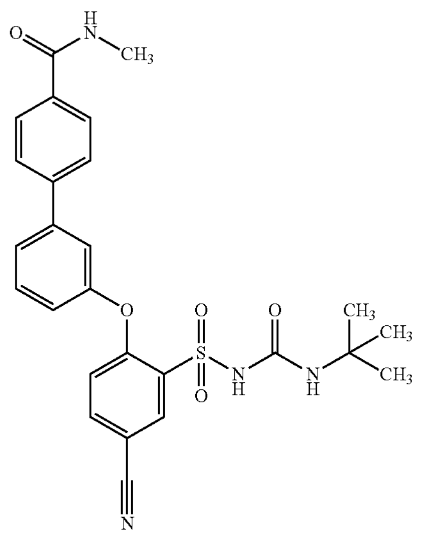

(X)

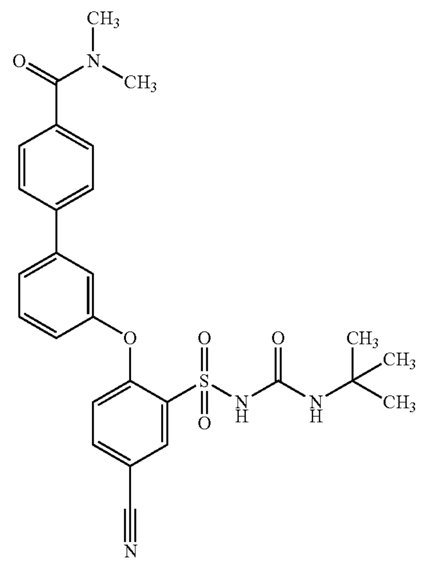

(XI)

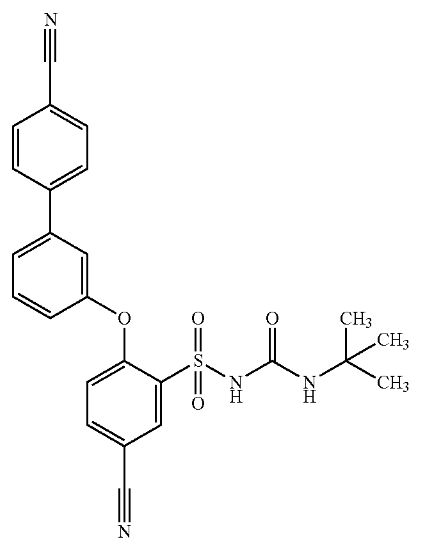

Substituted benzenesulfonyl ureas that may be used in formulations of the invention may be as described in U.S. Pat. Nos. 9,388,127; 9,522,877; 9,630,915; 9,738,599; 9,718,781; 9,932,304; 10,357,504; and 10,966,994 as well as in WO 2015/185989, all incorporated by reference.

Formulations of the invention may act as therapeutic drugs for pulmonary arterial hypertension, not only inhibiting the excessive vasoconstriction but also preventing the micro-thrombosis and, potentially, limit the pulmonary artery remodeling, right ventricular hypertrophy, endothelial cell dysfunction, fibrosis and local inflammation found in pulmonary arterial hypertension. Formulations of the invention may also directly suppress inflammation or proliferation pathways implicated in pulmonary arterial hypertension. Formulations of the invention may also antagonize or prevent the actions of 8-iso-prostaglandin $F_{2\alpha}$, a free-radical derived isoprostane generated in abundance in the clinical setting of pulmonary arterial hypertension, as well as in other diseases involving oxidative stress or injury and which mediates similar actions to T prostanoid thromboxane $A_2$, compounds of the invention will also antagonize these effects in pulmonary arterial hypertension. In addition, as T prostanoid thromboxane $A_2$ is a potent pro-inflammatory, pro-fibrotic and mitogenic agent promoting vascular remodeling, restenosis and/or hypertrophy and is the main cyclooxygenase-derived constrictor prostanoid within the lung, formulations of the invention may antagonize these effects. In addition, as 8-iso-prostaglandin $F_{2\alpha}$ is a potent pro-inflammatory, pro-fibrotic and mitogenic agent promoting vascular remodeling, restenosis and/or hypertrophy and is abundantly found or elevated in patients with pulmonary arterial hypertension, formulations of the invention may antagonize these effects.

Formulations of the invention display potent thromboxane $A_2$ receptor antagonist activity, for example inhibiting aggregation of human platelets ex vivo with an $IC_{50}$ of 1-10 nM. Formulations of the invention have excellent specificity, pharmacokinetic, pharmacodynamics, and toxicology profiles, including in treating Pulmonary Arterial Hypertension, thrombosis and cardiovascular diseases, renal disease, pulmonary disease, and breast, lung, prostate, bladder and other cancers.

Formulations of the present invention inhibit the actions of T prostanoid thromboxane $A_2$ and of the free-radical derived isoprostane 8-iso-prostaglandin (prostaglandin) $F_{2\alpha}$, in addition to certain other incidental ligands, for example the endoperoxide prostaglandin $G_2$/prostaglandin $H_2$ each of which act as agonists or partial agonists of the thromboxane $A_2$ receptor. The thromboxane $A_2$ receptor is expressed in a range of specific cell types throughout the body and its expression is altered in several disease indications. Formulations of the invention target the thromboxane $A_2$ receptors (including thromboxane $A_2$ receptor $\alpha$ and/or thromboxane $A_2$ receptor $\beta$) expressed in each of those cell types and in different disease settings, for example pulmonary arterial hypertension. Benzenesulfonyl urea of formulations of the invention may be used in the treatment of other diseases in which T prostanoid thromboxane $A_2$, 8-iso-prostaglandin $F_{2\alpha}$ or the thromboxane $A_2$ receptor itself have been implicated. These include, but are not limited to, various cardiovascular diseases (including thrombosis, various hypertensions including systemic and pregnancy induced hypertension, arterial peripheral disease), pulmonary diseases (including asthma, pulmonary hypertensions, pulmonary arterial hypertension, Chronic obstructive pulmonary disease, interstitial lung diseases, Idiopathic Pulmonary Fibrosis) and renal diseases (including glomerular nephritis and renal hypertension). The formulations of the invention also have applications in the treatment of prostate disease (such as benign prostate hyperplasia), various pro-inflammatory diseases (including, but not limited, to inflammatory cardiovascular, renal, pulmonary, post-viral/microbial infection) and neoplastic diseases (for example breast, lung or prostate cancers including Castrate-resistant prostate cancer).

The formulations of the invention may be used in any drug format, for example oral, intravenous, intraperitoneal, pulmonary, dermal, transdermal, delivery systems, intrathecal or on medical devices, such as pumps, slow-release pumps, stents or on drug-eluting stents. Advantageously, the formulations of the invention provide increased bioavailability for oral dose forms. In a preferred aspect of the invention, the formulation is formulated as an oral dose form.

The formulation may be in an oral dose form and the form may be a tablet, vial, sachet or capsule. The formulation may be in the form of powders, pellets, multi-particulates, beads, emulsions, spheres or any combinations, thereof. Oral solid dosage forms may be formulated as immediate release, controlled release, sustained (extended) release or modified release formulations.

The effective dosage of the formulation can readily be determined by a skilled person, having regard to typical factors such as the age, weight, sex and clinical history of the patient. A typical dosage could be, for example, 1-1,000 mg/kg, preferably 5-500 mg/kg per day, or less than about 5 mg/kg of benzenesulfonyl urea, for example administered once per day, multiple times per day, every other day, every few days, once a week, once every two weeks, or once a month, or a limited number of times, such as just once, twice or three or more times.

The formulations of the invention may be in a form suitable for oral use, for example, as tablets, troches, lozenges, fast-melts, sachets, aqueous or oily suspensions, dispersible powders or granules, emulsions, hard or soft capsules, or syrups or elixirs. Formulations intended for oral use may be prepared according to any method known in the art for the manufacture of formulations and such compositions may contain one or more agents selected from sweetening agents, flavoring agents, coloring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets or capsules may be uncoated or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, and 4,265,874, to form osmotic therapeutic tablets for control release. Preparation and administration of compounds is discussed in U.S. Pat. No. 6,214,841 and U.S. Pub. 2003/0232877, each incorporated by reference.

Formulations for oral use may also be presented as hard gelatin capsules in which the active ingredient is mixed with an inert solid diluent, for example calcium carbonate, calcium phosphate or kaolin, or as soft gelatin capsules in which the active ingredient is mixed with water or an oil medium, for example peanut oil, liquid paraffin or olive oil.

An alternative oral formulation, where control of gastrointestinal tract hydrolysis of the compound or active ingredient is sought, can be achieved using a controlled-release formulation, where a compound of the invention is encapsulated in an enteric coating, for example an enteric coating comprising a complex of a drug comprising a substituted benzenesulfonyl urea and a vinylpyrrolidone-vinyl acetate copolymer.

Aqueous suspensions may contain the formulation in admixture with excipients suitable for the manufacture of aqueous suspensions. Such excipients are suspending agents, for example sodium carboxymethylcellulose, methylcellulose, hydroxypropyl methylcellulose, sodium alginate, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the formulation in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These formulations may be preserved by the addition of an anti-oxidant such as ascorbic acid.

Dispersible powders and granules suitable for preparation of an aqueous suspension by the addition of water provide the formulation in admixture with a dispersing or wetting agent, suspending agent and one or more preservatives. Suitable dispersing or wetting agents and suspending agents are exemplified, for example sweetening, flavoring and coloring agents, may also be present.

The formulation of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The formulations may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

The formulation may also be administered in the form of suppositories for rectal administration of the drug. These formulations can be prepared by mixing the formulation with a suitable non-irritating excipient which is solid at ordinary temperatures but liquid at the rectal temperature and will therefore melt in the rectum to release the drug. Examples of such materials are cocoa butter and polyethylene glycols.

The formulation can be tuned to vary the particles sizes thereby facilitating delivery in various formats, for example through the pulmonary route. Advantageously, the formulation may be suitable for administration via the pulmonary route, such as an inhalable, aerosol or using a nebulizer-system. Advantageously, the formulations may have applications in a wide variety of disease settings.

Formulations of the invention may be scaled-up in manufacture and may be suitable for use through oral administration in humans. Scaled-up manufacture of formulations of the invention provided high quality formulations in an efficient, reproducible and robust chemical process. Formulations of the invention are suitable for industrial manufacture and may comply with Good Manufacturing Practice procedures & International Council for Harmonisation regulatory guidelines.

In aspects of the invention, the polymer in formulations of the invention may be a vinylpyrrolidone-vinyl acetate copolymer. Vinylpyrrolidone-vinyl acetate copolymer is a linear copolymer produced by the free-radical polymerization of vinylpyrrolidone and vinyl acetate. The ratio of vinylpyrrolidone to vinyl acetate in the vinylpyrrolidone-vinyl acetate copolymer may be a ratio in the range of 7:3 to 3:7 vinylpyrrolidone to vinyl acetate.

The vinylpyrrolidone-vinyl acetate copolymer may be a vinylpyrrolidone-vinyl acetate copolymer as sold by BASF SE, of Ludwigshafen, Germany, for example the product sold under the trademark KOLLIDON VA64. The vinylpyrrolidone-vinyl acetate copolymer may comprise a vinylpyrrolidone:vinyl acetate in a ratio of 6:4. The vinylpyrrolidone-vinyl acetate copolymer may be as described in Bühler, 2009, Kollidon: Polyvinylpyrrolidone excipients for the pharmaceutical industry, BASF SE Pharma Ingredients & Services, 9th ed., available at the website of BASF SE under product guides for the product sold as KOLLIDON VA64, the contents of which are incorporated by reference herein.

Vinylpyrrolidone-vinyl acetate copolymer is a copolymer used as a soluble binder for granulation, as dry-binder in direct compression technology, as a film-forming agent in sprays, as pore-former in coating, in taste-masking applications, and as a solubilizer in hot melt extrusion processes. Vinylpyrrolidone-vinyl acetate copolymers readily dissolve in all hydrophilic solvents, and solutions of more than 10% concentration can be prepared in water, ethanol, isopropanol, methylene chloride, glycerol and propylene glycol. Vinylpyrrolidone-vinyl acetate copolymers may be less soluble in ether, cyclic, aliphatic and alicyclic hydrocarbons. Advantageously, vinylpyrrolidone-vinyl acetate copolymers may be more cost effective than natural binders.

In aspects of the invention, the polymer in formulations of the invention may be a dimethylaminoethyl methacrylate-copolymer. Dimethylaminoethyl methacrylate-copolymer is a copolymer produced by the polymerization of acrylic and methacrylic acids or their esters. Certain embodiments include a cationic copolymer based on dimethylaminoethyl methacrylate, butyl methacrylate, and methyl methacrylate. For example, the polymer may have the IUPAC name: Poly(butyl methacrylate-co-(2-demethylaminoeethyl) methacrylate-co-methyl methacrylate) 1:2:1, a dimethyl-aminoethyl methacrylate-copolymer. Such a polymer may be characterized by low viscosity, high pigment binding capacity, good adhesion, and low polymer weight gain. Embodiments have the CAS number 24938-16-7 and the INCI name: Acrylates/Dimethylaminoethyl Methacrylate Copolymer. Certain embodiments use the dimethylaminoethyl methacrylate-copolymer as sold under the trademark EUDRAGIT® EPO by Evonik Industries AG (Essen, Germany). The EUDRAGIT® EPO (EE) cationic polymer has a mean relative molecular mass of about 150,000, is prepared by copolymerization of butyl methacrylate, 2-dimethylaminoethylmethacrylate, and methyl methacrylate. The ratio of dimethylaminoethyl methacrylate groups to butyl methacrylate and methyl methacrylate groups is about 2:1:1. See Chang, 2009, Polymethacrylates, monograph at pp. 525-533 of Handbook of Pharmaceutical Excipients, 6Ed, Rowe et al., Eds., Pharmaceutical Press (London, UK), incorporated by reference.

Dimethylaminoethyl methacrylate-copolymer is a copolymer used as film coating, melt, wet or dry granulation, hot melt extrusion, micro-encapsulation and spray drying.

Formulation of the invention may be amorphous solid dispersions. A solid dispersion is a dispersion of one or more hydrophobic active ingredients in a hydrophilic inert carrier at solid state. Solid dispersions may be prepared, for example, by melting, solvent evaporation, a fusion method, kneading method, melting method, spray drying method, co-grinding method, lyophilization technique, hot melt extrusion, melt agglomeration, or supercritical fluid technology. An amorphous solid dispersion is a molecular system comprising an active pharmaceutical ingredient stabilized by an excipient, commonly a polymer, to produce a system with improved physical stability when compared with an amorphous active pharmaceutical ingredient. In an amorphous solid dispersion, the system preferably does not show evidence of crystallinity.

The formulation may comprise a spray dried dispersion. A spray dried dispersion is a dispersion formed by co-precipitating an active pharmaceutical ingredient with a polymer in a stable amorphous solid dispersion. Spray drying may improve dissolution rates and enhance the bioavailability of poorly soluble compounds.

Spray dried dispersions may be formed by first creating a solvent solution of the substituted benzenesulfonyl urea and the polymer. This may be done by weighing the required amount of benzenesulfonyl urea and adding it to the solvent solution and mechanically mixing the solution, weighing the polymer and adding the polymer to the benzenesulfonyl urea-solvent solution and mechanically mixing the solution. In aspects of the invention, the solvent may be acetone. In aspects of the invention, the acetone comprises greater than 90% of the solvent solution. In aspects of the invention the solvent may be dicholomethane:methanol in a ratio of 3:1.

The solution may then be spray dried creating a substituted benzenesulfonyl urea: polymer bulk intermediate.

Spray drying may be conducted at a high an inlet temperature, for example a temperature of about or greater than 80 degrees C. and an outlet temperature of about 45 degrees C. The spray drying may be conducted with an evaporation temperature of about 55 or 60 degrees C.

The bulk intermediate may then be subject to secondary drying, forming a spray solid dispersion powder. Spray solid dispersion powders provide the advantage of being easily packaged in a primary container or delivery vehicle. Secondary drying may be conducted by a rotary dryer to evaporate residual solvent, for example acetone if acetone was used as the solvent. In preferred aspects of the invention, the spray solid dispersion formulation comprises less than 5,000 ppm solvent.

In alternative aspects of the invention, the amorphous solid dispersion formulation may be formed in a solvent-free hot melt extrusion. In a hot melt extrusion, the drug and polymer are melted and mixed together to form an amorphous solid in the absence of solvent. Advantageously, in a hot melt extrusion process, because of the absence of solvent the introduction of water is reduced or eliminated from the manufacturing process.

In another alternative aspect of the manufacturing process, a solvent/surfactant process may be used to form the formulation of the invention. In a solvent/surfactant process a Self-Emulsifying Drug Delivery System or Self-Micro Emulsifying-Drug Delivery System (SMEDDS) is used to encapsulate the formulation of the present invention within a hydrophobic phase surrounded by a hydrophilic phase comprising a surfactant. The hydrophilic phase may also comprise a co-solvent, particularly in SMEDDS processes.

The formulation may comprise a spray dried dispersion of the drug comprising the substituted benzenesulfonyl urea and a pharmaceutically acceptable vinylpyrrolidone-vinyl acetate copolymer copolymer, such as the vinylpyrrolidone-vinyl acetate copolymer sold by BASF SE, headquartered in Ludwigshafen, Germany, for example the product sold under the trademark KOLLIDON® VA64. The ratio of the benzenesulfonyl urea drug to vinylpyrrolidone-vinyl acetate copolymer may be 1:4. For example, the formulation may comprise a compound of formula (IV):

(IV)

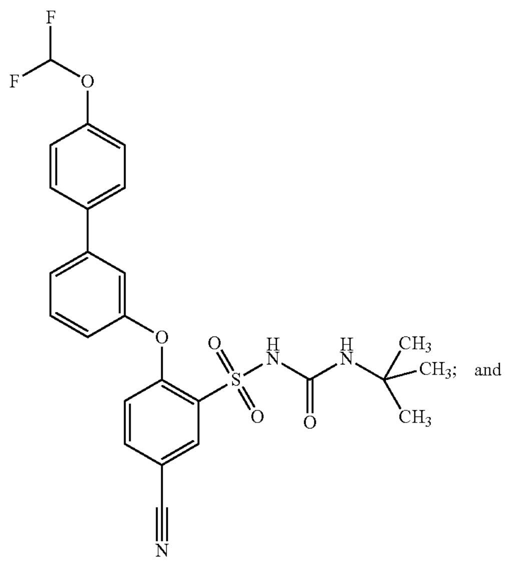

and a vinylpyrrolidone-vinyl acetate in a ratio of 1:4 compound of formula (IV) to vinylpyrrolidone-vinyl acetate copolymer.

An advantage of the formulation approach of the present invention, for example spray solid dispersion formulations, is that the vinylpyrrolidone-vinyl acetate copolymer may form a unique complex with the benzenesulfonyl urea drug and in so doing confer a protection to the benzenesulfonyl urea, shielding or masking it from the low pH of the stomach (for example, as can be simulated through drug dissolution studies in Fasted State Simulated Gastric Fluid (FaSSGF) with a pH ~1.6), maintaining it in a benzenesulfonyl urea: vinylpyrrolidone-vinyl acetate copolymer complex until it is subsequently released on passage to the higher pH of the small intestine (for example, as simulated in Fasted State Simulated Intestinal Fluid (FaSSIF) with a pH ~6.5). Advantageously, the benzenesulfonyl urea in a benzenesulfonyl urea:vinylpyrrolidone-vinyl acetate copolymer spray solid dispersion formulation would be protected from the acidic environment of the stomach (~pH 1.6), would not release the drug from the drug-polymer complex into the stomach gastric fluid itself but would disperse the drug from the drug-polymer complex in the higher pH environment of the intestine where it may be maximally absorbed.

Formulation of the invention may be more insoluble in lower pH environments than in higher pH environments. A low pH environment is a pH lower than about 5. For example, formulations of the invention may be substantially insoluble at a pH of less than 2. A high pH environment is a pH environment above 5. For example, formulations of the invention may be substantially soluble at a pH above 5.3.

Solubility is the amount of a substance that will dissolve in a given amount of another substance, for example a solvent. The solvent may be water or may be gastric fluid of the stomach or gastric fluid of the intestine.

Substantially insoluble may mean that less than 10% of the formulation or benzenesulfonyl urea dissolves in a solvent in 75 minutes. Substantially insoluble may mean that less than 30% of the formulation or benzenesulfonyl urea dissolves in a solvent in 75 minutes. Substantially insoluble may mean that less than 30% of the formulation or benzenesulfonyl urea dissolves in a solvent in 90 minutes. Substantially soluble may mean that greater than 60% of the formulation dissolves in a solvent in 25 minutes or less than 25 minutes. Substantially soluble may mean that greater than 60% of the formulation dissolves in a solvent in less than 20 minutes. Substantially soluble may mean that greater than 60% of the formulation dissolves in a solvent in less than 15 minutes. Substantially soluble may mean that greater than 60% of the formulation dissolves in a solvent in less than 10 minutes. Substantially soluble may mean that greater than 70% of the formulation dissolves in a solvent in 25 minutes.

Formulations of the invention can be used to treat human diseases in which human thromboxane $A_2$ receptors and prostanoid receptors play a role. Formulations of the invention can be used to treat human diseases where there is altered expression in the levels of the human thromboxane $A_2$ receptors. Formulations of the invention can be used to treat human diseases in which there are elevated levels of T prostanoid thromboxane $A_2$. Formulations of the invention can be used to treat human diseases in which there are elevated levels of other biochemical entities/ligands (for example prostaglandin $G_2$/prostaglandin $H_2$, 20-Hydroxyeicosatetraenoic acid or isoprostanes including 8-iso prostaglandin $F_{2\alpha}$) that act through the human thromboxane $A_2$ receptors. Formulations of the invention can be used to treat human diseases in which there is elevated levels of non-enzymatic, free-radical derived isoprostanes that signal through the human thromboxane $A_2$ receptors such as 8-iso-prostaglandin $F_{2\alpha}$. Formulations of the invention can be used to antagonize the thromboxane $A_2$ receptor for use in the treatment of pulmonary arterial hypertension. Formulations of the invention can be used to treat thrombosis, either alone or in combination with other therapeutic agents. Formulations of the invention can be used to treat micro-vessel thrombosis, either alone or in combination with other therapeutic agents. Formulations of the invention can be used to treat other cardiovascular diseases, including those cardiovascular diseases associated with types 1 and 2 diabetes mellitus. Examples of fields of application, but not limited to, include treatment of various cardiovascular diseases including prevention of excessive platelet aggregation associated atherothrombosis, ischemic stroke, transient ischemic attach (TIA), acute coronary syndrome. For these conditions, formulations of the invention can be used either alone or in combination with other therapeutics drugs. Formulations of the invention can be used to treat other pulmonary diseases, including but not limited to asthma, pulmonary hypertensions, pulmonary arterial hypertension, interstitial lung diseases, idiopathic pulmonary fibrosis and used either alone or in combination with other therapeutics drugs. Formulations of the invention can be used to treat renal diseases and used either alone or in combination with other therapeutics drugs. Formulations of the invention can be used to treat prostate diseases including, but not limited to benign prostate hyperplasia and either alone or in combination with other therapeutics drugs. Formulations of the invention can be used to treat inflammatory diseases, and either alone or in combination with other therapeutics drugs. Formulations of the invention can be used to treat neoplastic diseases including cancers, and may be used either alone or in combination with other therapeutics drugs. Formulations of the invention can be used to treat stroke and transient ischemic attack, and may be used either alone or in combination with other therapeutics drugs. Formulations of the invention can be used in combination with immune modulators to treat cancers. Formulations of the invention can be used to treat dysregulated smooth muscle cell function, such as but not limited to various types of hypertension and restenosis post-surgical stenting. Formulations of the invention can be used to treat dysregulated endothelial cell function.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The invention provides for the manufacture and biological evaluation of formulations of benzenesulfonyl urea and vinylpyrrolidone-vinyl acetate copolymer that act as antagonists of the thromboxane $A_2$ receptor $\alpha$ and/or thromboxane $A_2$ receptor $\beta$ (iso) forms of the human thromboxane $A_2$ receptor, also referred to as the T prostanoid receptor. These thromboxane $A_2$ receptor antagonists will inhibit the actions (antagonize) of the receptor and of the free radical derived isoprostane 8-iso-prostaglandin (prostaglandin) $F_{2\alpha}$, and of all other incidental agents (e.g the endoperoxide prostaglandin $G_2$/prostaglandin $H_2$ and 20-Hydroxyeicosatetraenoic acid) that activate (act as agonists or as partial agonists) of the thromboxane $A_2$ receptor. The thromboxane $A_2$ receptor is expressed in a range of cell types throughout the body and the compounds (thromboxane $A_2$ receptor antagonists) described herein target the thromboxane $A_2$ receptors (including thromboxane $A_2$ receptor $\alpha$ and/or thromboxane $A_2$ receptor $\beta$) expressed in all of those cell types. In addition, altered expression of the thromboxane $A_2$ receptors occurs in a range of disease settings and the compounds (thromboxane $A_2$ receptor antagonists) described herein target the thromboxane $A_2$ receptors (including thromboxane $A_2$ receptor $\alpha$ and/or thromboxane $A_2$ receptor $\beta$) expressed in all of those cell types and in different disease settings including in inflammation and in cancer. Furthermore, the compounds can be used in oral formulations.

Example 1: Assessment of NTP42:KVA4 Dissolution Rates

Formulations comprising the drug comprising the substituted benzene sulfonurea of formula IV (hereinafter referred to as NTP42) and the vinylpyrrolidone-vinyl acetate copolymer were successfully created. The vinylpyrrolidone-vinyl acetate copolymer was a vinylpyrrolidone-vinyl acetate sold by BASF SE, headquartered in Ludwigshafen, Germany, under the trademark KOLLIDON® VA64 (hereinafter "KVA". Using an Amorphous Solid Dispersion approach, a Spray-Dried Dispersion, a formulation with the pharmaceutically acceptable vinylpyrrolidone-vinyl acetate copolymer KVA with an NTP42:polymer ratio of 1:4, referred to as NTP42:KVA4 was created. The formulations were tested for dissolution.

FIG. 1 shows the dissolution rate of two batches of NTP42:KVA4 in biorelevant Fasted State Simulated Intestinal Fluid (FaSSIF; pH 6.5). Samples (10 mg) of NTP42:KVA4 from 2 demonstration batches, referred to as PSD-1, Batch #1 and PSD-1, Batch #2, were placed in hydroxypropyl methylcellulose capsules and their dissolution ability assessed in FaSSIF, pH 6.5 media. At time-points, samples of the media were taken for High Performance Liquid Chromatography (HPLC) analysis to determine the amount of NTP42 released from the spray solid dispersion. Data presented are the mean values from 3 independent dissolution experiments for each spray solid dispersion, plus or minus the standard error of the mean (SEM).

In detailed follow-on studies, including in pH switch studies aimed at evaluating the dissolution of NTP42:KVA4 in biorelevant media with different pH simulating different stages of drug passage through the gastrointestinal tract, NTP42 was released into media at ≥pH 4, where it did not crystallize or precipitate and remained as the desired amorphous drug product.

Figure 2:
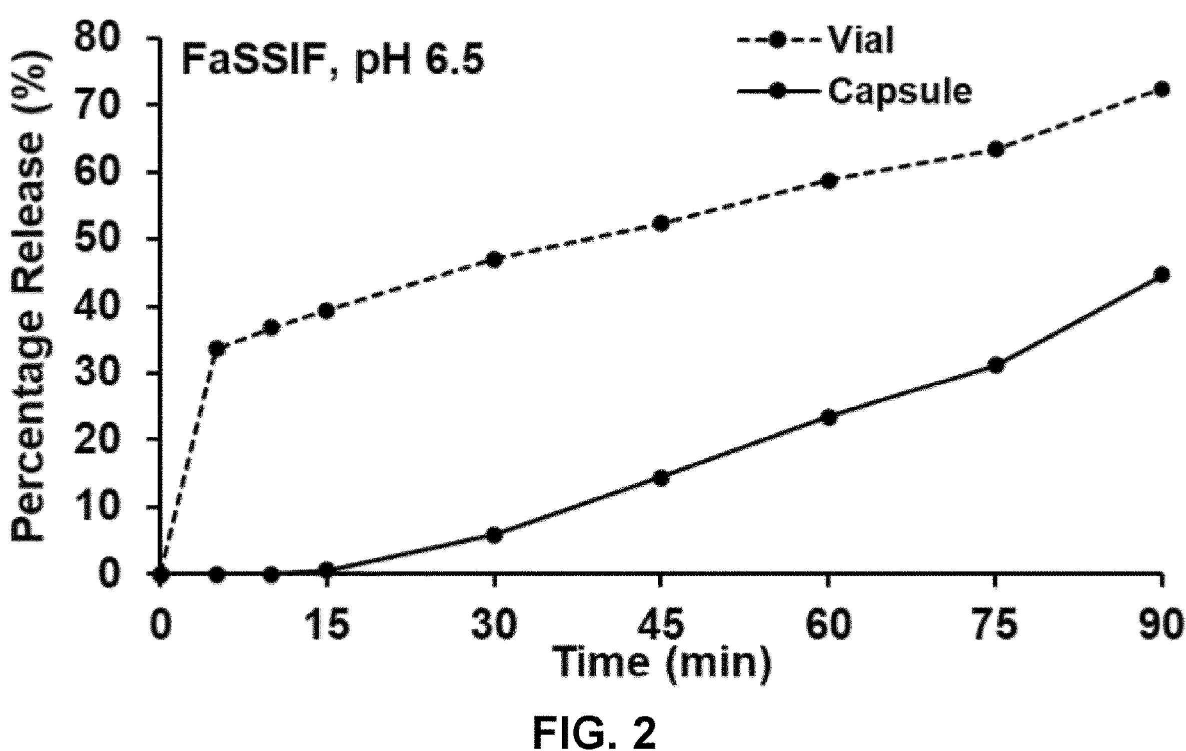
FIG. 2 shows a graph of the release rate of a formulation of the present invention.

FIG. 2 shows a graph of the dissolution rate of NTP42:KVA4 in at a pH of 6.5. Samples (10 mg) of NTP42:KVA4 were placed in hydroxypropyl methylcellulose capsules (solid line) or in vials (broken line) and their dissolution assessed in FaSSIF, pH 6.5 alone. At the time-points indicated samples of the media were taken for HPLC analysis to determine the amount of NTP42 released from the spray solid dispersion.

Figure 3:
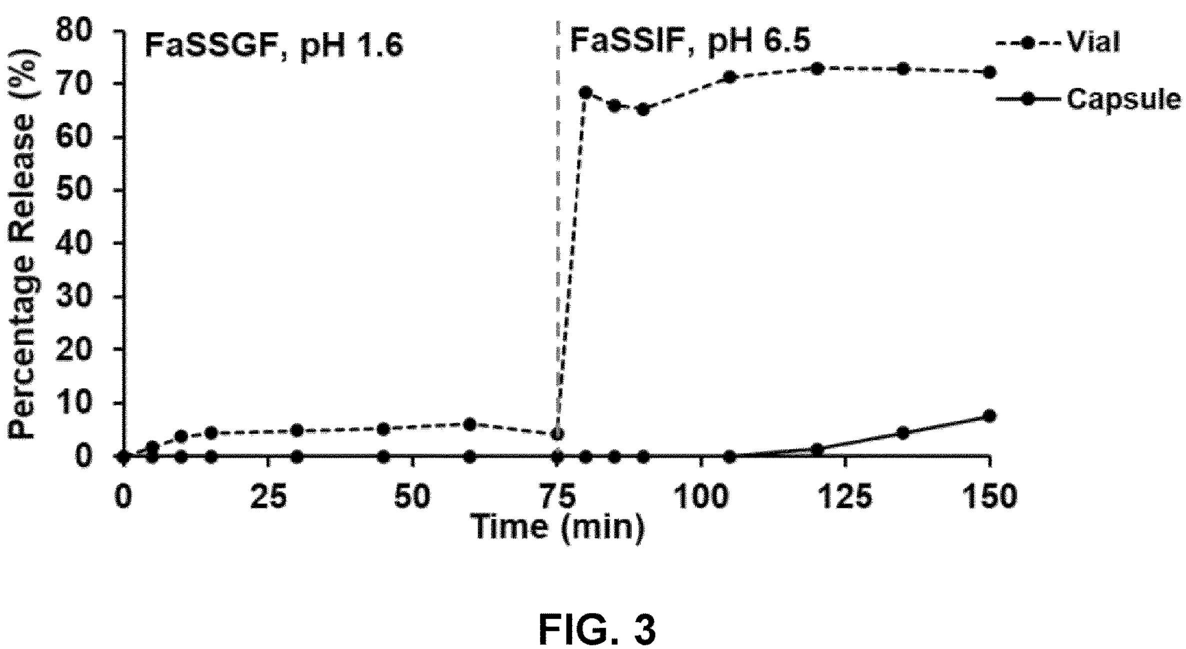
FIG. 3 shows a graph of the release rate of a formulation of the present invention.

FIG. 3 shows a graph of the dissolution rate of NTP42:KVA4 first at a pH of 1.6 with the pH changed at 75 minutes to a pH of 6.5. Samples (10 mg) of NTP42:KVA4 were placed in hydroxypropyl methylcellulose capsules (solid line) or in vials (broken line) and their dissolution assessed in biorelevant Fasted State Simulated Gastric Fluid (FaSSGF), pH 1.6 media initially, followed by a switch to the FaSSIF, pH 6.5 media. At the time-points indicated samples of the media were taken for HPLC analysis to determine the amount of NTP42 released from the spray solid dispersion.

Figure 4:
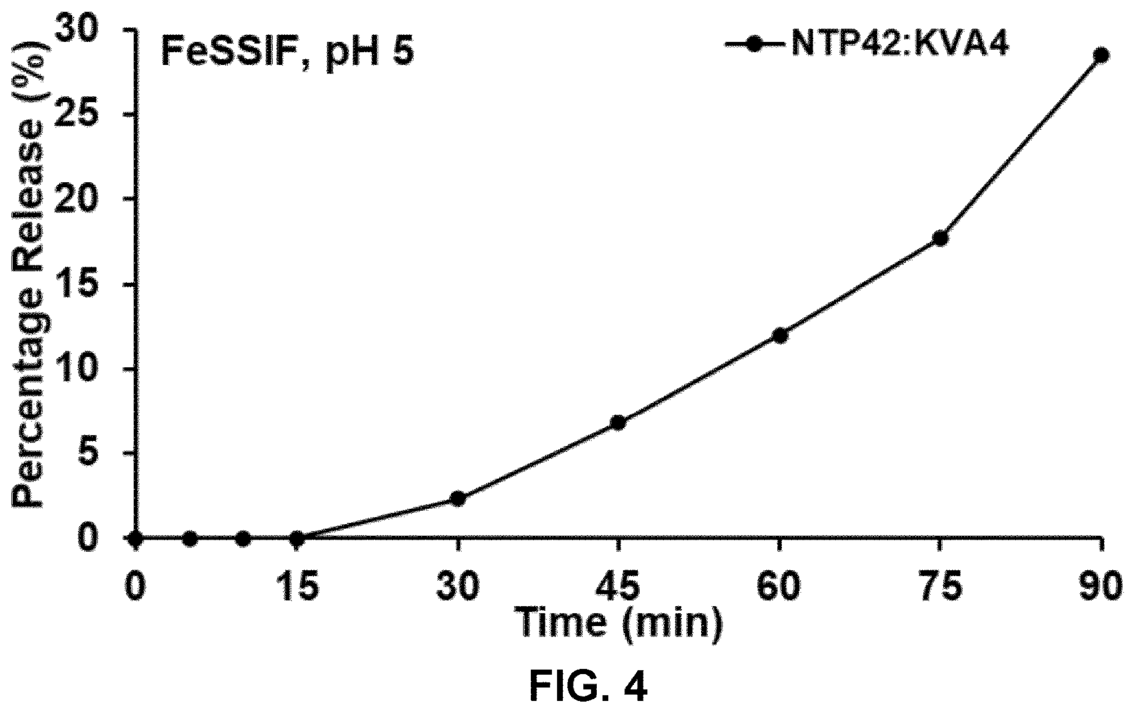
FIG. 4 shows a graph of the release rate of a formulation of the present invention.

FIG. 4. shows a graph of the dissolution rate of NTP42:KVA4 at a pH of 5. Samples (10 mg) of NTP42:KVA4 were placed in hydroxypropyl methylcellulose capsules and their dissolution assessed in biorelevant Fed State Simulated Intestinal Fluid (FeSSIF), pH 5 alone. At the time-points indicated samples of the media were taken for HPLC analysis to determine the amount of NTP42 released from the spray solid dispersion.

Figure 5:
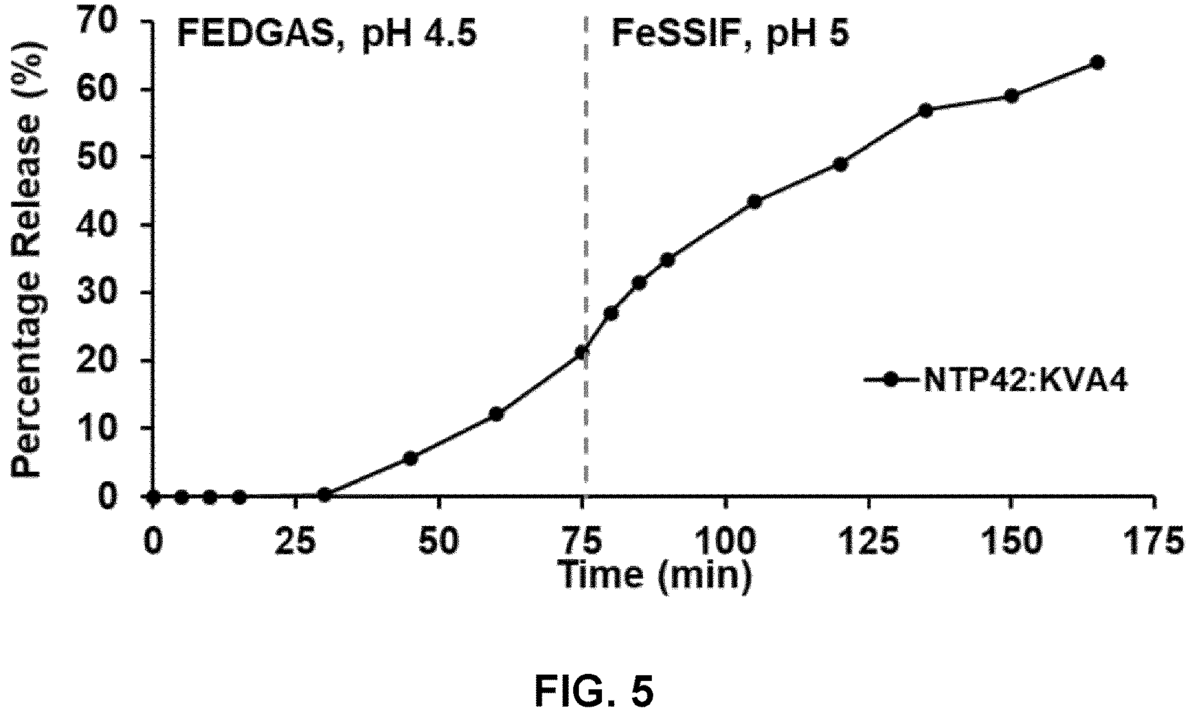
FIG. 5 shows a graph of the release rate of a formulation of the present invention.

FIG. 5 shows a graph of the dissolution rate of NTP42:KVA4 first at a pH of 4.5 with the pH changed at 75 minutes to a pH of 5. Samples (10 mg) of NTP42:KVA4 were placed in hydroxypropyl methylcellulose capsules and their dissolution assessed in Fed Gastric Dissolution Media (FEDGAS), pH 4.5 media initially, followed by a switch to the FeSSIF, pH 5 media. At the time-points indicated samples of the media were taken for HPLC analysis to determine the amount of NTP42 released from the spray solid dispersion.

As shown, dissolution of NTP42:KVA4 did not occur in low pH, i.e., in FaSSGF, pH 1.6. Vinylpyrrolidone-vinyl acetate copolymer is highly water-soluble where its solubility is independent of pH. Therefore, the lack of dissolution of NTP42:KVA4 in FaSSGF, pH 1.6 was surprising. Moreover, in the pH switch from FaSSGF, pH 1.6 to FaSSIF, pH 6.5 studies, NTP42 was rapidly released from NTP42:KVA4, indicating that the vinylpyrrolidone-vinyl acetate copolymer confers a protective effect on NTP42, shielding it from the low pH of FaSSGF, pH 1.6 and maintaining it in complex for release at higher pH, e.g., FaSSIF, pH 6.5.

Example 2: Rat Pharmacokinetic (PK) Studies

NTP42:KVA4 was evaluated in rat pharmacokinetic studies, which confirmed excellent bioavailability and NTP42 drug exposure when administered to animals orally both as a "Drug-in-Bottle" suspension formulation or as a "Drug-in-Capsule." NTP42 was administered by IV (1 mg/kg) in a dosing vehicle composed of DMSO, Cremophor-EL and PBS (10%: 10%: 80% v/v/v ratio). For the assessments of spray solid dispersion formulations as 'Drug-in-Bottle' and 'Drug-in-Capsule' formats in in vivo rat pharmacokinetic studies, spray-dried material was filled into (ii) gelatin and (iii) hydroxypropyl methylcellulose capsules for the 'Drug-in-Capsule' format and was compared to (i) 'Drug-in-Bottle' format, where spray solid dispersion material was administered as a suspension in 0.5% hydroxypropyl methylcellulose-E3 (w/v) dosing vehicle. Note that rats were fasted 16 hr prior to administration of drug.

Results are shown in FIG. 6 which shows Table 1, a Summary of Pharmacokinetic Data for NTP42:KVA4 Delivered to Orally to Fasted Rats as "Drug-in-Bottle" Suspension or as a "Drug-in-Capsule". Data presented are the mean values from 4 independent animals from each administration group. In Table 1, AUC means Area Under Curve; Cmax, means maximum plasma concentration of NTP42; HPMC means hydroxypropyl methylcellulose; IV means Intravenous; and Tmax means time taken for NTP42 plasma concentration to reach Cmax.

Example 3: Polymer Dissolution Comparison

Formulations of NTP42 and the polymers a vinylpyrrolidone-vinyl acetate as sold by BASF SE, headquartered in Ludwigshafen, Germany, for example the product sold under the trademark KOLLIDON® VA64 (abbreviated as "KVA"), the polymer sold by Evonik Industries AG, headquartered in Essen, Germany under the trademark EUDRAGIT® EPO (hereinafter "EPO"), the polymer Hydroxypropyl Methylcellulose, the polymer Hydroxypropyl Methylcellulose Acetate Succinate, and the polymer sold by Evonik Industries AG, headquartered in Essen, Germany under the trademark EUDRAGIT® L100 were tested. Polymers were tested alone or in the presence of plasticizers, for example, polyethylene glycol and the polyoxyl 40 hydrogenated castor oil or macroglycerol hydroxystearate sold under the trademark KOLLIPHOR RH40.

Figure 7:
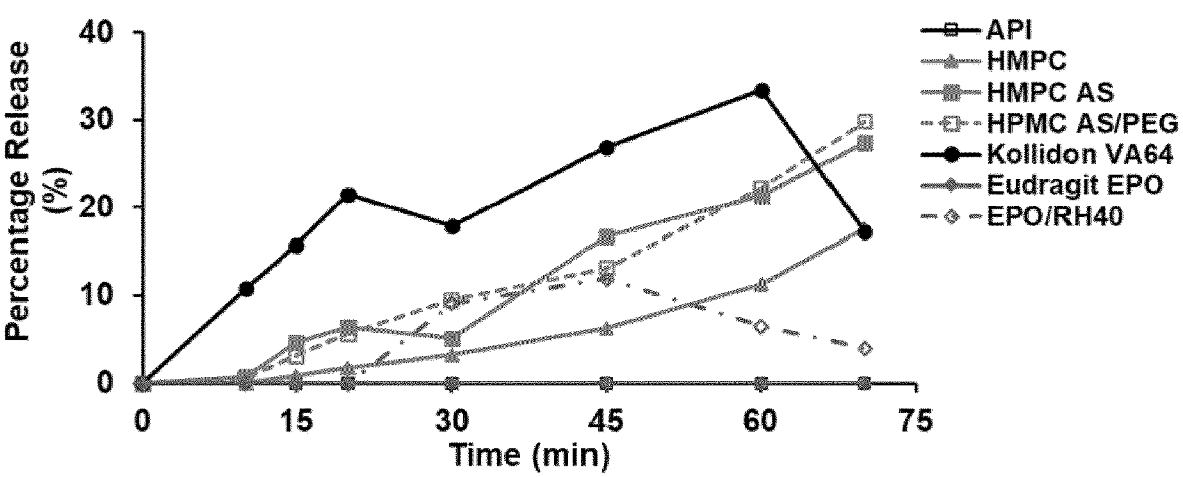
FIG. 7 shows release rate of formulations of benzenesulfonyl urea and polymers.

FIG. 7 shows a graph of the dissolution rate of the formulations. Samples of each amorphous solid dispersion formulation were placed in baskets and their dissolution ability assessed in phosphate buffer, pH 6.5 alone. At the time-points indicated, samples of the media were taken for HPLC analysis to determine the amount of NTP42 released from the amorphous solid dispersion. Graphs are representative of 3 independent dissolution experiments for each amorphous solid dispersion.

All NTP42: polymer formulations produced amorphous material. Low levels of degradation for formations comprising KVA and EPO were found and selected for further study.

Dissolution of formulations of NTP42 and KVA at ratios of 1:1, 1:4, 1:8 NTP42:KVA were compared to formulations of NTP42 and EPO at ratios of 1:4, 1:9, and 1:19 NTP42:EPO. Additionally, formulations with the inclusion of the excipient Syloid to reduce the level of exposure of the formulations to moisture during the spray drying process were evaluated at ratios of 1:1:4 NTP42:Syloid:KVA64 and 1:1:4 NTP42:Syloid:EPO.

Figure 8:
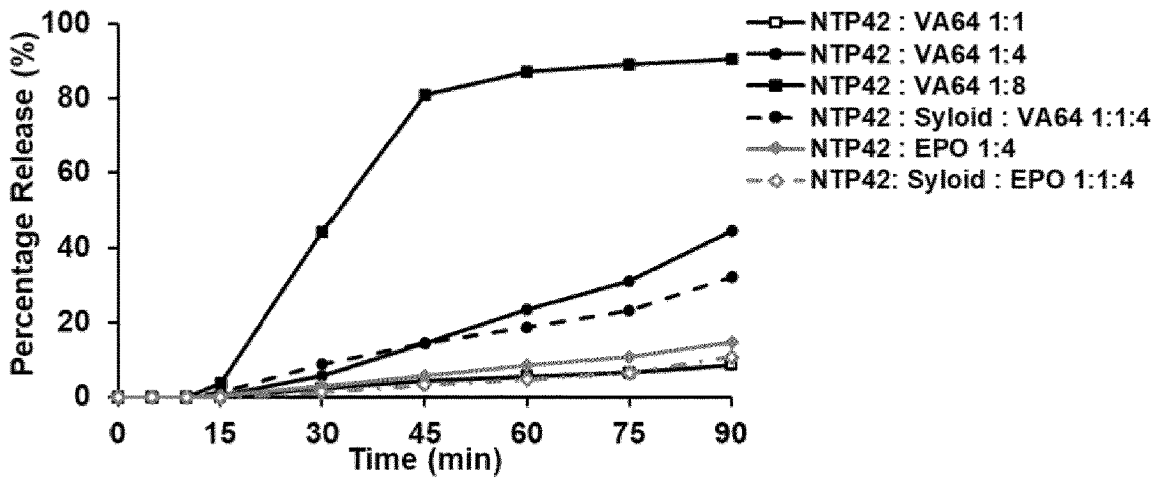
FIG. 8 shows release rate of formulations of benzenesulfonyl urea and polymers.

FIG. 8 shows a graph of the dissolution rate of the formulations. Samples of each spray solid dispersion formulation were placed in hydroxypropyl methylcellulose capsules and their dissolution ability assessed in FaSSIF, pH 6.5 media alone. At the time-points indicated, samples of the media were taken for HPLC analysis to determine the amount of NTP42 released from the spray solid dispersion. Graphs are representative of 3 independent dissolution experiments for each spray solid dispersion.

Figure 9:
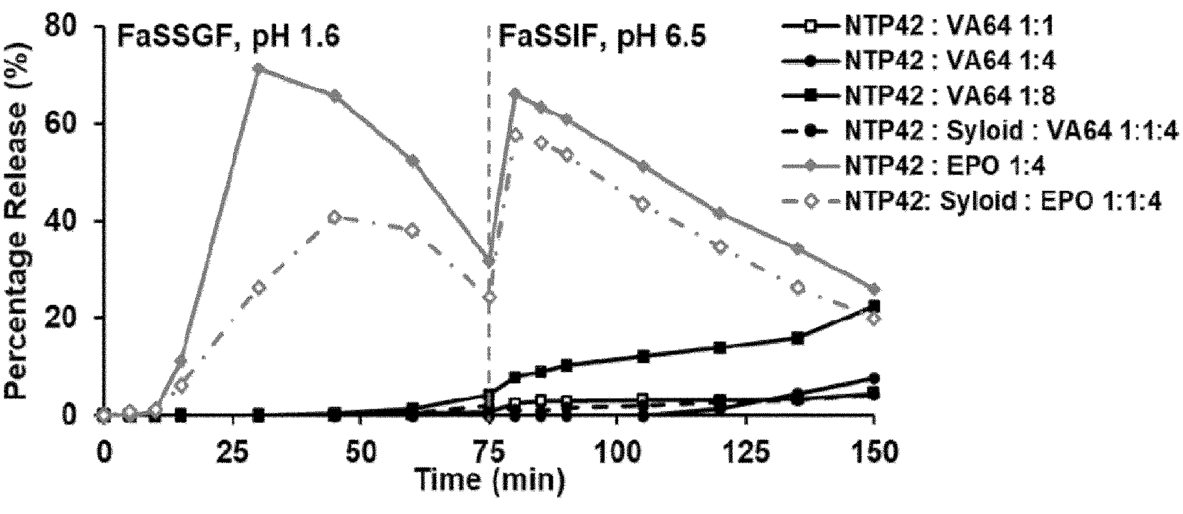
FIG. 9 shows release rate of formulations of benzenesulfonyl urea and polymers.

FIG. 9 shows a graph of the dissolution rate of the formulations. Samples of each spray solid dispersion formulation were placed in hydroxypropyl methylcellulose capsules and their dissolution ability assessed in FaSSGF, pH 1.6 media initially, followed by a switch to the FaSSIF, pH 6.5 media. At the time-points indicated, samples of the media were taken for HPLC analysis to determine the amount of NTP42 released from the spray solid dispersion. Graphs are representative of 3 independent dissolution experiments for each spray solid dispersion.

As shown, the SSD formulations were evaluated for dissolution in the biorelevant FaSSIF (pH 6.5) and in pH switch experiments, where dissolution was assessed in FaSSGF (pH 1.6) media followed by a switch to FaSSIF, pH 6.5. Maximum dissolution of NTP42 (≥80%) in FaSSIF, pH 6.5 was observed for NTP42: vinylpyrrolidone-vinyl acetate copolymer at drug:polymer ratio 1:8. With respect to the pH switch evaluations, maximal dissolution of the EPO based spray solid dispersion formulations was observed in the FaSSGF pH 1.6 media with ~80% release of NTP42.

However, after ~30 min, re-crystallization occurred as indicated by the rapid decrease of NTP42 present in the media. Moreover, while there was an increase in dissolution with the switch in pH from the FaSSGF, pH 1.6 to the FaSSIF, pH 6.5, this was transient and a decline in soluble NTP42 was observed.

While there was no dissolution of the vinylpyrrolidone-vinyl acetate copolymer based spray solid dispersion formulations in low pH, dissolution occurred in the FaSSIF (pH 6.5) media. The solubility of vinylpyrrolidone-vinyl acetate copolymer is not dependent on pH and therefore, the lack of dissolution of NTP42 in the FaSSGF (pH 1.6) media was surprising. Moreover, while reduced compared to that which occurred in FaSSIF, pH 6.5 alone, dissolution occurred following the pH switch.

In light of the exciting dissolution data in the FaSSIF (pH 6.5), where almost 100% dissolution of NTP42 was observed with the NTP42:KVA at the 1:8 drug:polymer ratio, and the surprising finding of the lack of dissolution of the vinylpyrrolidone-vinyl acetate copolymer based spray solid dispersions in the FaSSGF (pH 1.6), further dissolution studies were performed comparing the NTP42:KVA at the 1:4 and 1:8 drug:polymer ratio.

These included the following investigations:

(i) Repeat dissolutions in FaSSIF (pH 6.5) and in the pH switch from the biorelevant FaSSGF, pH 1.6 to FaSSIF (pH 6.5) media, where the dissolution of spray solid dispersion material in capsules was compared to that of the powder in vials.

(ii) Dissolutions in Fed-State Simulated Intestinal Fluid (FeSSIF; pH 5.0) and in the pH switch from the biorelevant Fed Gastric Dissolution Media (FEDGAS, pH 4.5) to FeSSIF (pH 5.0) media.

Figure 10:
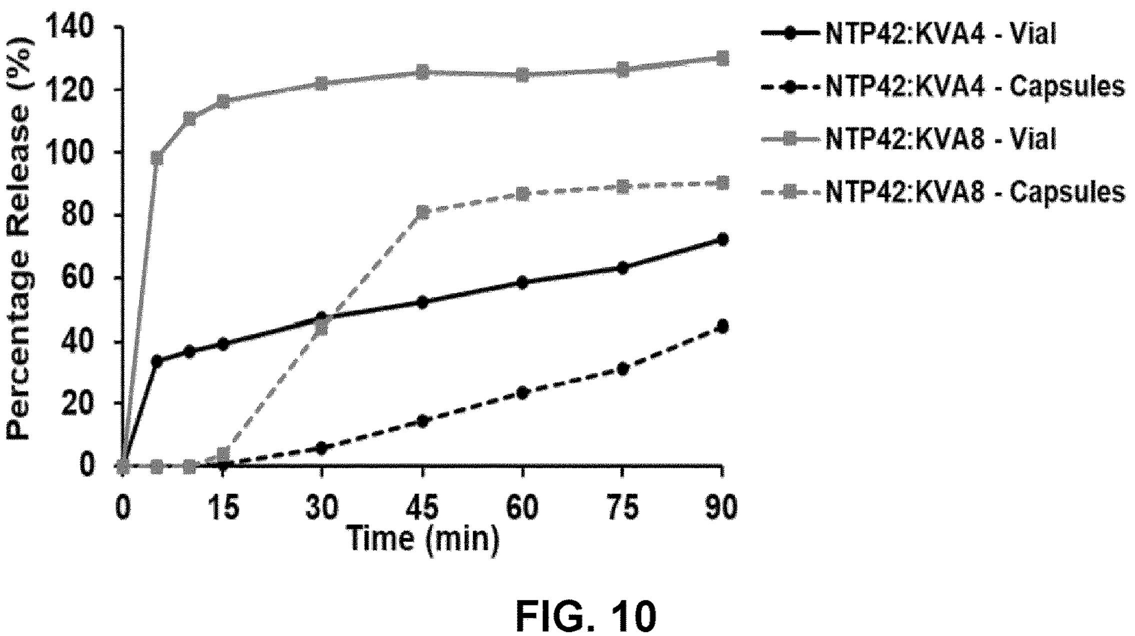
FIG. 10 shows a graph of the release rate of formulations of the present invention.

FIG. 10 shows a graph of the dissolution rate of NTP42 from NTP42:KVA formulations in FaSSGF. Samples of the NTP42:KVA at the 1:4 (NTP42:KVA4) and 1:8 (NTP42:KVA8) drug:polymer ratio formulation were placed in vials (solid lines) or for comparison, in hydroxypropyl methylcellulose capsules (broken lines) and their dissolution ability assessed in FaSSIF, pH 6.5 media alone. At the time-points indicated samples of the media were taken for HPLC analysis to determine the amount of NTP42 released from the spray solid dispersion. Graphs are representative of 3 independent dissolution experiments for each spray solid dispersion.

Figure 11:
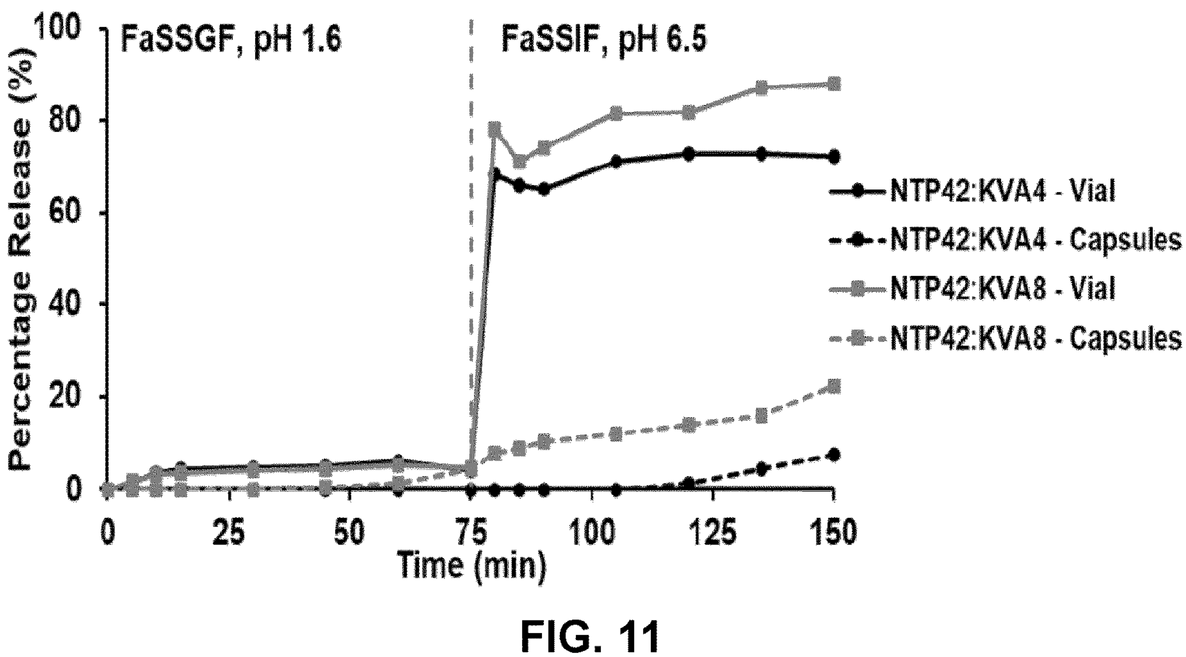
FIG. 11 shows a graph of the release rate of formulations of the present invention.

FIG. 11 shows a graph of the dissolution rate of NTP42:KVA formulations in FASSGF to FASSIF studies. Samples of the NTP42:KVA at the 1:4 (NTP42:KVA4) and 1:8 (NTP42:KVA8) drug:polymer ratio formulation were placed in vials (solid lines) or for comparison, in hydroxypropyl methylcellulose capsules (broken lines) and their dissolution ability assessed in FaSSGF, pH 1.6 media initially, followed by a switch to the FaSSIF, pH 6.5 media. At the time-points indicated samples of the media were taken for HPLC analysis to determine the amount of NTP42 released from the spray solid dispersion. Graphs are representative of 3 independent dissolution experiments for each spray solid dispersion.

Consistent with findings of the NTP42 and EPO comparative studies, dissolution of both the NTP42:KVA spray solid dispersion formulations occurred in the FaSSIF media alone, where the extent of dissolution was greater for the spray solid dispersion powder in vials compared to that of the powder in capsules. In the pH switch dissolution studies, maximal dissolution of both the NTP42:KVA formulations was observed, where a significant improvement was observed for the NTP42:KVA at 1:4 ratio. These dissolutions studies confirmed that the KVA confers a protection of NTP42, protecting it from the acid environment of the stomach (i.e., FaSSGF, pH 1.6) maintaining it in complex for release at higher pH, e.g., FaSSIF, pH 6.5.

Figure 12:
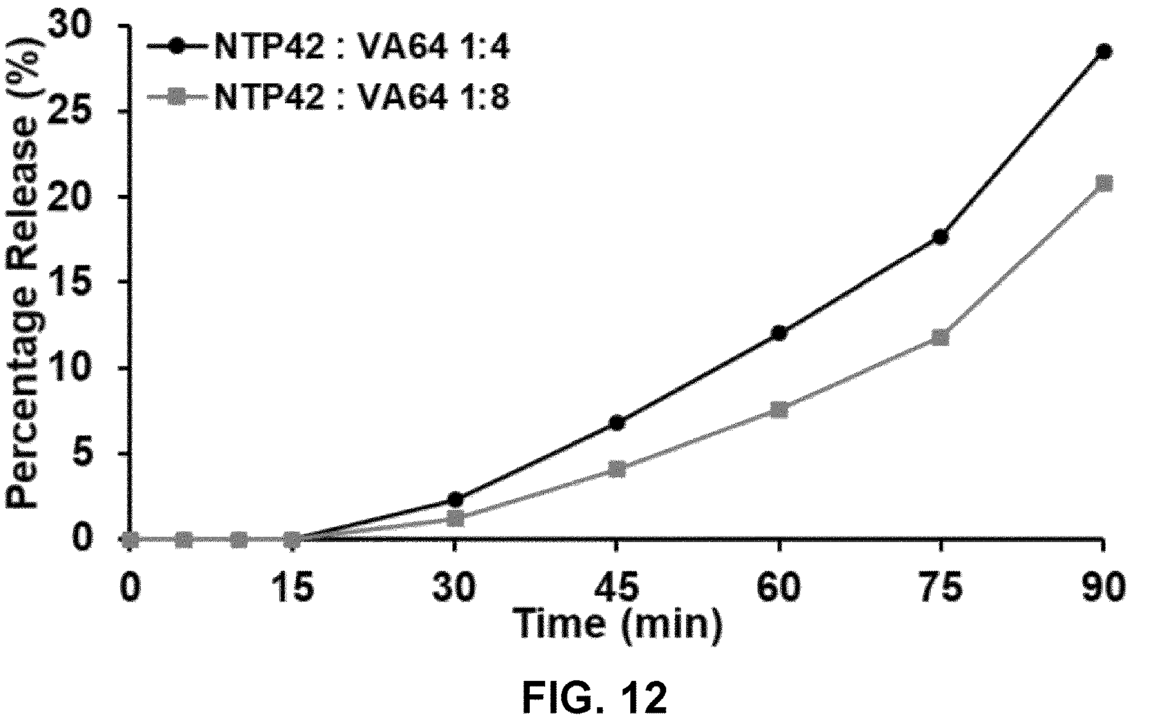
FIG. 12 shows a graph of the release rate of formulations of the present invention.

FIG. 12 shows a graph of the dissolution rate of NTP42:KVA formulations in FeSSIF, pH 5. Samples of the NTP42:KVA at the 1:4 (NTP42:KVA4) and 1:8 (NTP42:KVA8) drug:polymer ratio formulation were placed in hydroxypropyl methylcellulose capsules and their dissolution ability assessed in FeSSIF, pH 5 media alone. At the time-points indicated, samples of the media were taken for HPLC analysis to determine the amount of NTP42 released from the spray solid dispersion. Graphs are representative of 3 independent dissolution experiments for each spray solid dispersion.

Figure 13:
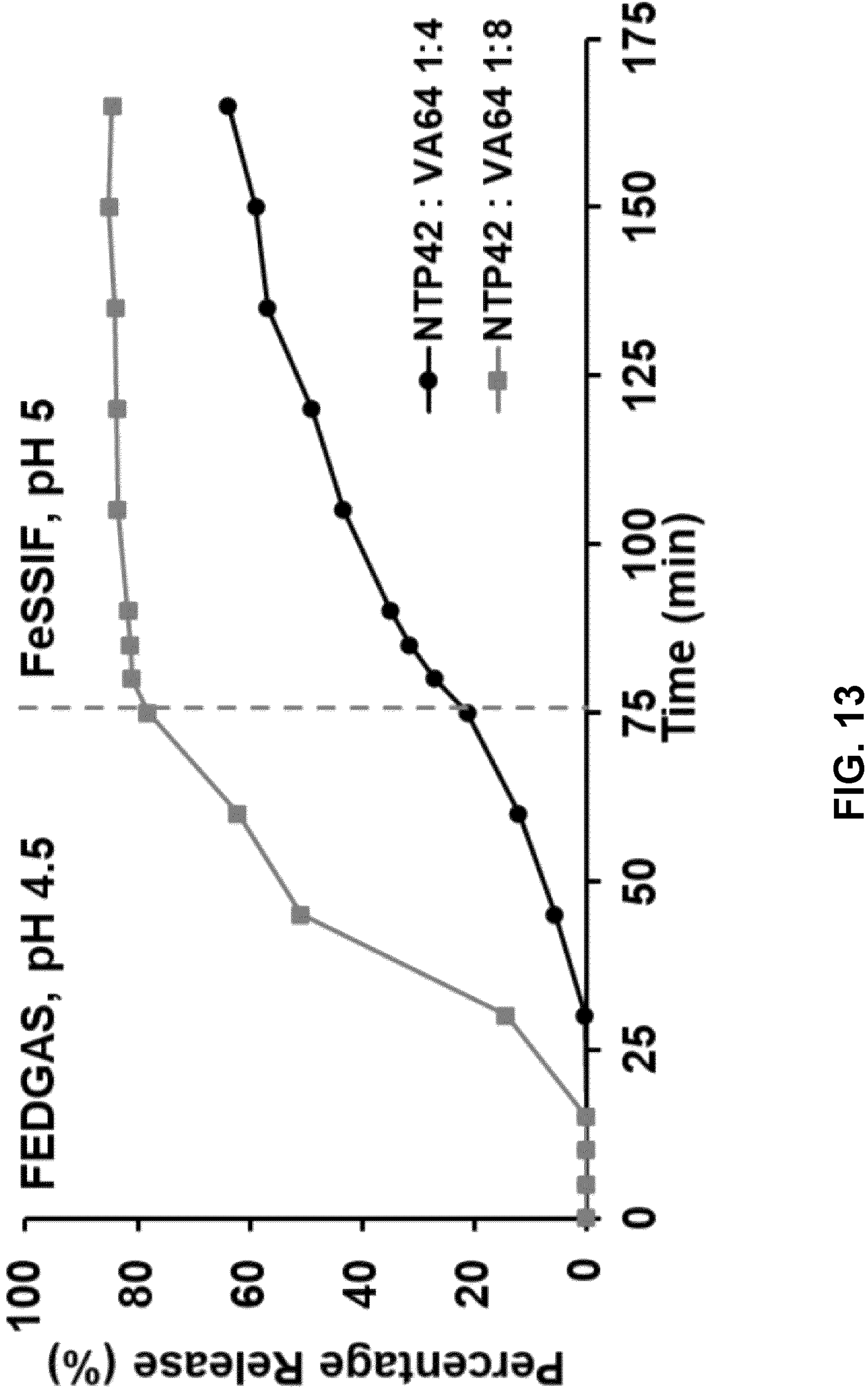
FIG. 13 shows a graph of the release rate of formulations of the present invention.

FIG. 13 shows a graph of the dissolution rate of NTP42:KVA formulations in FEDGAS, pH 4.5 to FeSSIF, pH 5 studies. Samples of the spray solid dispersion formulations, NTP42:KVA at the 1:4 and 1:8 drug:polymer ratio were placed in hydroxypropyl methylcellulose capsules and their dissolution ability assessed in FeSSIF, pH 5 alone. At the time-points indicated, samples of the media were taken for HPLC analysis to determine the amount of NTP42 released from the spray solid dispersion. Graphs are representative of 3 independent dissolution experiments for each spray solid dispersion.

In the FeSSIF media (pH 5), dissolution of NTP42:KVA4 was greater than that of NTP42:KVA8, while in the lower pH of FEDGAS (pH 4.5) dissolution of NTP42:KVA4 was slower than that of NTP42:KVA8.

Example 4: Rat Pharmacokinetic (PK) Studies for Polymer Comparison

In addition, the NTP42:KVA spray solid dispersion formulations at the 1:4 and 1:8 drug:polymer ratio were confirmed to provide good exposure after oral delivery to rats in PK studies. NTP42 was administered by IV (1 mg/kg) in a dosing vehicle composed of DMSO, Cremophor-EL and PBS (10%: 10%: 80% v/v/v ratio). For the assessment of spray solid dispersion formulations as 'Drug-in-Bottle' format in in vivo rat pharmacokinetic (PK) studies, spray-dried material was administered in dosing vehicle, 0.5% hydroxypropyl methylcellulose-E3.

FIG. 14 gives Table 2, a Summary of Pharmacokinetic Data for NTP42:KVA4 at the 1:4 and 1:8 drug polymer ratio. Data presented are the mean values from 4 independent animals from each administration group. In Table 2, AUC means Area Under Curve; Cmax, means maximum plasma concentration of NTP42; IV means Intravenous; and Tmax means time taken for NTP42 plasma concentration to reach Cmax.

Example 5: Human Oral Dosage Studies

NTP42:KVA4 is administered in an oral dosage form to human subjects. NTP42:KVA4 is found to be suitable for oral administration. NTP42:KVA4 is protected in the low pH of the stomach, remaining intact as a drug:polymer complex, but ready for dissolution at the higher pH of the intestine for maximal absorption.

Example 6: Demonstration of the In Vivo Efficacy of NTP42:KVA4 in the Rat Monocrotaline (MCT) Model of Pulmonary Arterial Hypertension (PAH)

NTP42:KVA4 is evaluated in pre-clinical efficacy studies in the monocrotaline (MCT) model of pulmonary arterial hypertension (PAH), where data is presented in these examples.

NTP42, as a non-formulated drug, has shown efficacy in both the monocrotaline-(MCT) and Sugen5416/Hypoxia-(Su/Hx)-induced models of PAH in rats. See Mulvaney et al. BMC Pulmonary Medicine (2020) 20:85 & Mulvaney et al. Eur J Pharmacol (2020) 889:173658, both incorporated by reference.

Following the development and manufacture of the formulated drug product, NTP42:KVA4, the MCT-induced PAH rat model was used to demonstrate its efficacy in a pre-clinical model of PAH. MCT is a toxin known to selectively cause pulmonary artery injury characterised by endothelial and vascular damage, in situ thrombosis and development of pulmonary edema. Remodelling of the damaged endothelial and vascular cells is responsible for the narrowing/obliteration of the vascular lumen, thus limiting the blood flow through the pulmonary arteries and increasing pulmonary arterial pressure (PAP). This in turn augments the right ventricular (RV) afterload, leading to the development of a marked RV hypertrophy in MCT-treated rats.

To assess the efficacy of NTP42 when delivered as the oral formulation NTP42:KVA4 in the MCT-induced model of PAH, rats received a single subcutaneous injection of MCT (60 mg/kg) solution or saline (No MCT) at the start of the study.

Figure 15:
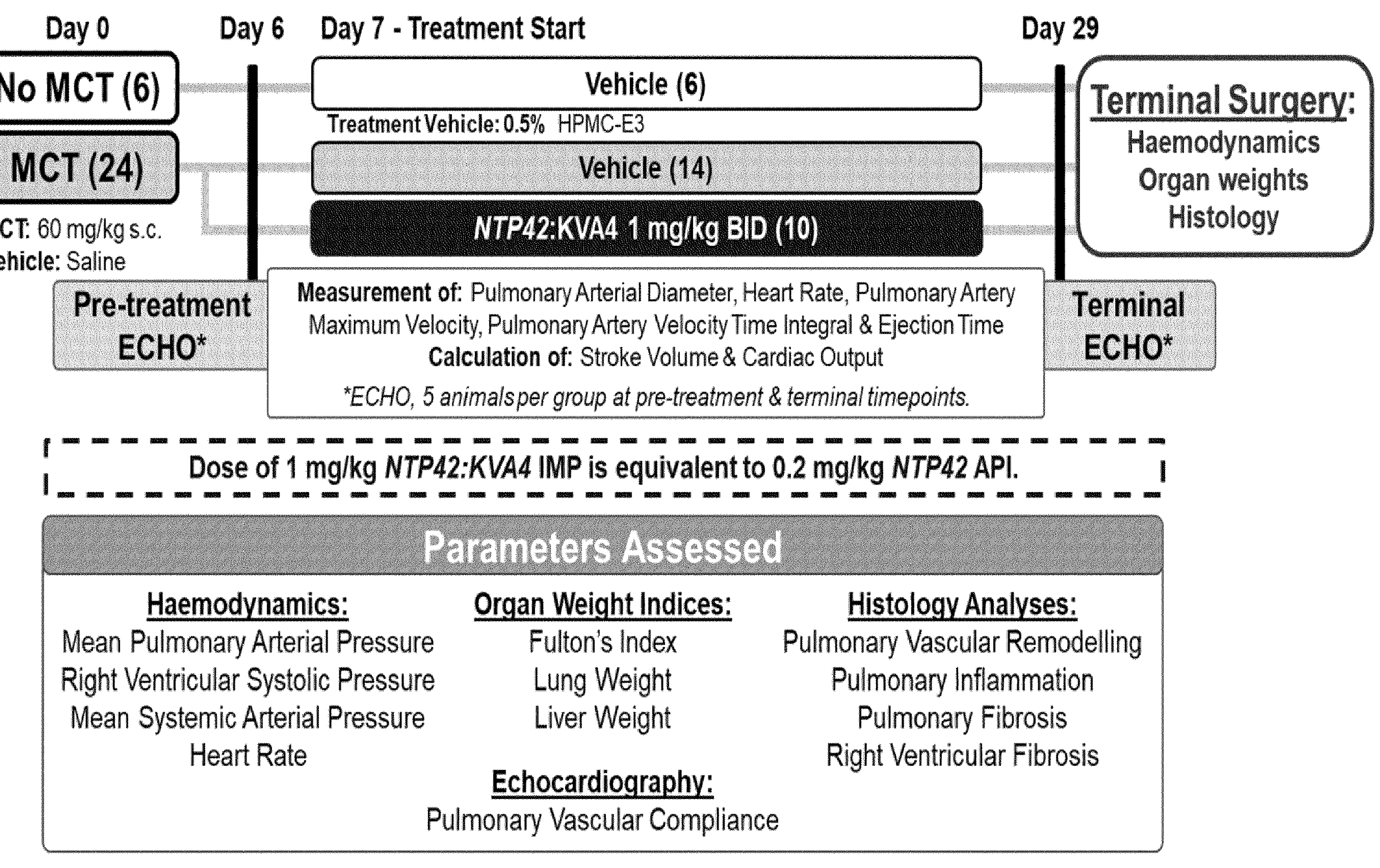
FIG. 15 diagrams experimental design for a pre-clinical efficacy study.

FIG. 15 diagrams experimental design for a pre-clinical efficacy study in the rat monocrotaline (MCT)-induced Pulmonary Arterial Hypertension (PAH) Model.

At day 0, male Sprague-Dawley rats (7 to 9 weeks old & weighing 284 g to 424 g) were either injected subcutaneously with a single dose of monocrotaline (MCT; 60 mg/kg), or as control saline (No MCT).

Drug treatment was initiated on Day 7 where animals were treated twice daily (BID) for 22 days with either NTP42:KVA4 (1 mg/kg), or as negative control, the placebo (30 mg/kg BID KOLLIDON VA 64). All treatments were administered by oral gavage as a suspension in 0.5% (w/v) hydroxypropyl methylcellulose (HPMC).

At Day 29, post-MCT induction, rats were anaesthetized for cardiac surgery and haemodynamic parameters recorded. Baseline echocardiogram (ECHO) assessments were carried out on five randomly selected animals from each group on Day 6 and on Day 29 prior to terminal haemodynamic surgery.

On the day of surgery (Day 29), hemodynamic parameters (systemic arterial, right ventricular and pulmonary blood pressures; and heart rate) were recorded in anesthetized rats. Thereafter, lungs and hearts were removed and weighed. The left lung was flushed with saline and then perfused with 10% non-buffered formalin (NBF). The heart was excised to facilitate measurement of the right ventricle (RV) and left ventricle plus septum to determine the Fulton's Index. Within the lung, histological analyses were performed of pulmonary vascular remodeling (morphometric vessel measurement and α-smooth muscle actin (SMA) expression), pulmonary inflammation (CD68+ macrophages), and pulmonary fibrosis (Masson's Trichrome staining). Within the RV, additional histological analysis was performed of cardiac fibrosis (Masson's Trichrome staining).

The data, presented in FIG. 16-FIG. 25 and FIG. 26, demonstrate that NTP42:KVA4 (1 mg/kg, BID) offers significant treatment benefit, reducing the severity of MCT-induced PAH across multiple disease parameters.

Figure 16:
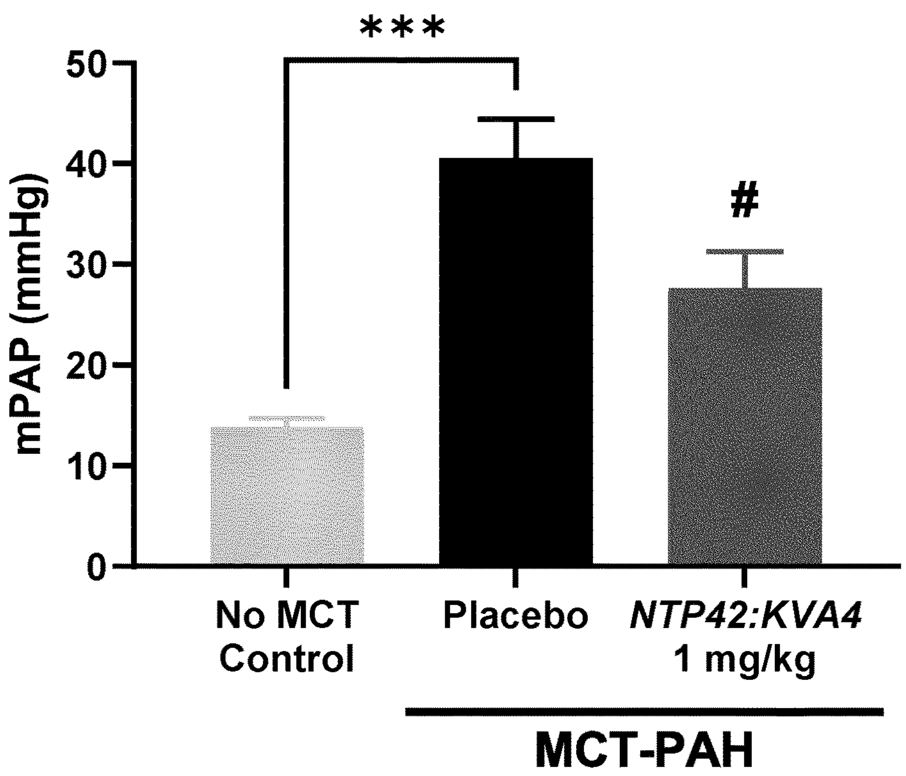
FIG. 16 gives results showing Mean Pulmonary Arterial Pressure (mPAP).
Figure 17:
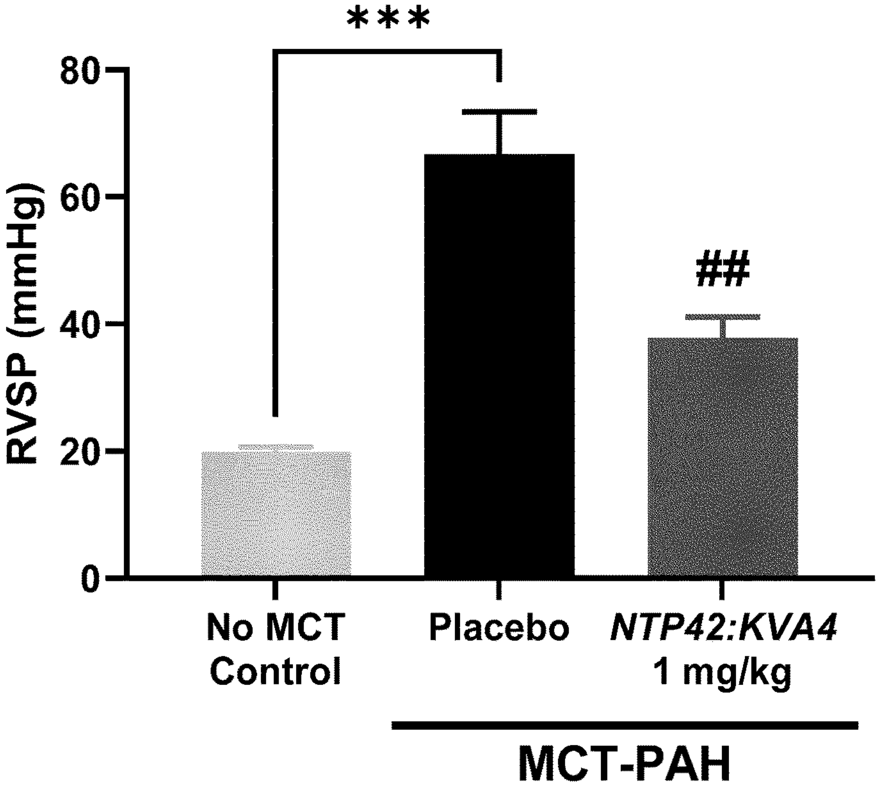
FIG. 17 gives results showing Right Ventricular Systolic Pressure (RVSP).

This includes reduction of the MCT-induced increases in the haemodynamic measurements of mean pulmonary artery pressure (mPAP; FIG. 16) and right ventricular systolic pressure (RVSP; FIG. 17) with no deleterious effects on either the systemic mean arterial pressure (mAP, FIG. 18) or heart rate (HR, FIG. 19). NTP42:KVA4 significantly reduced MCT-induced vascular remodeling as assessed through two histological methods, morphometric measurements (FIG. 20) and α-smooth muscle actin expression (FIG. 21).

Figure 27:
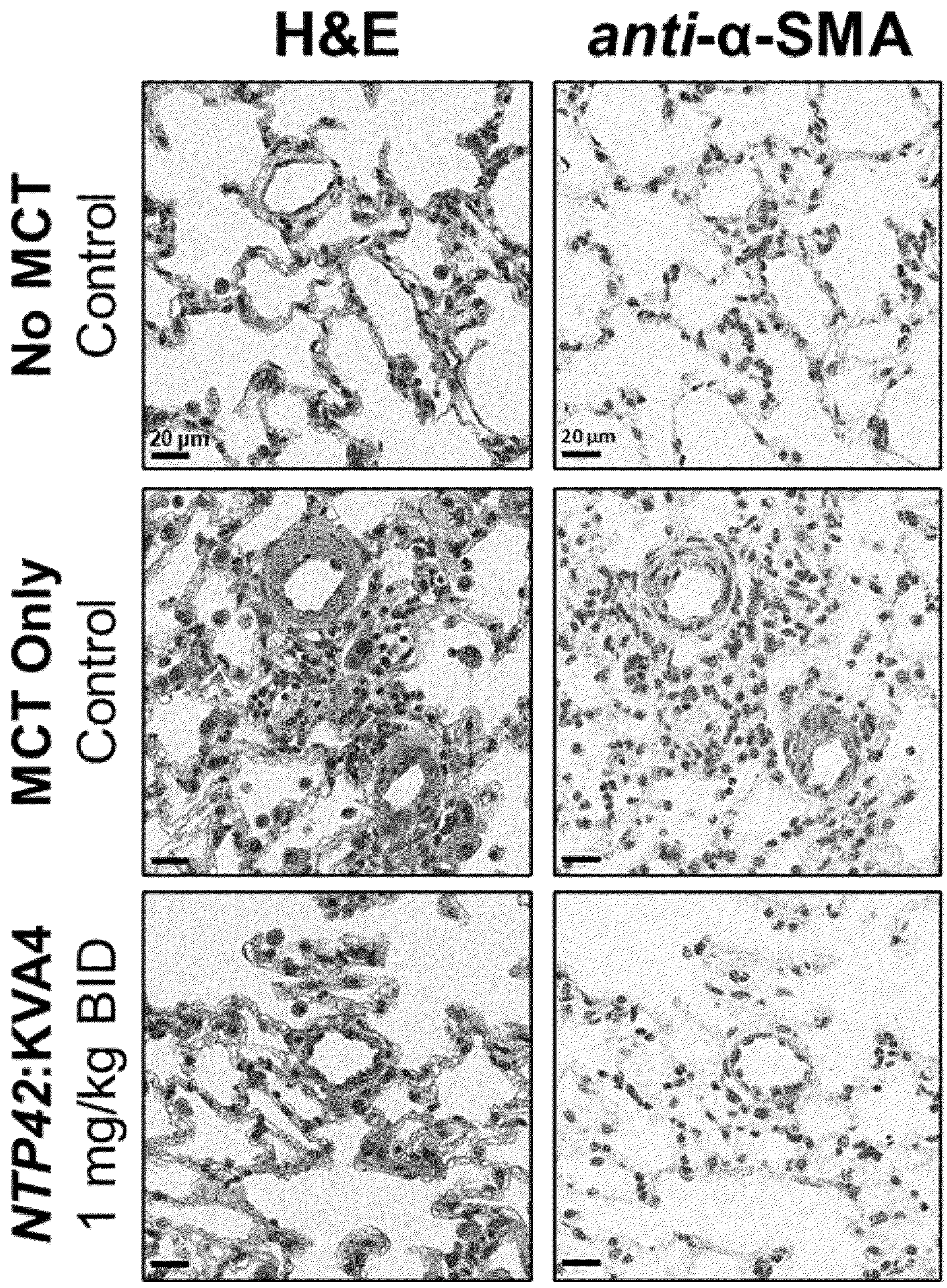
FIG. 27 presents lung tissue sections showing pulmonary vascular remodeling.

Representative histology for H&E- and α-SMA-stained lung tissue are shown in FIG. 27, where treatment with NTP42:KVA4 resulted in tissues that appeared similar to those of the non-diseased (No MCT Control) and substantially healthier than the MCT Only Placebo Control.

Figure 22:
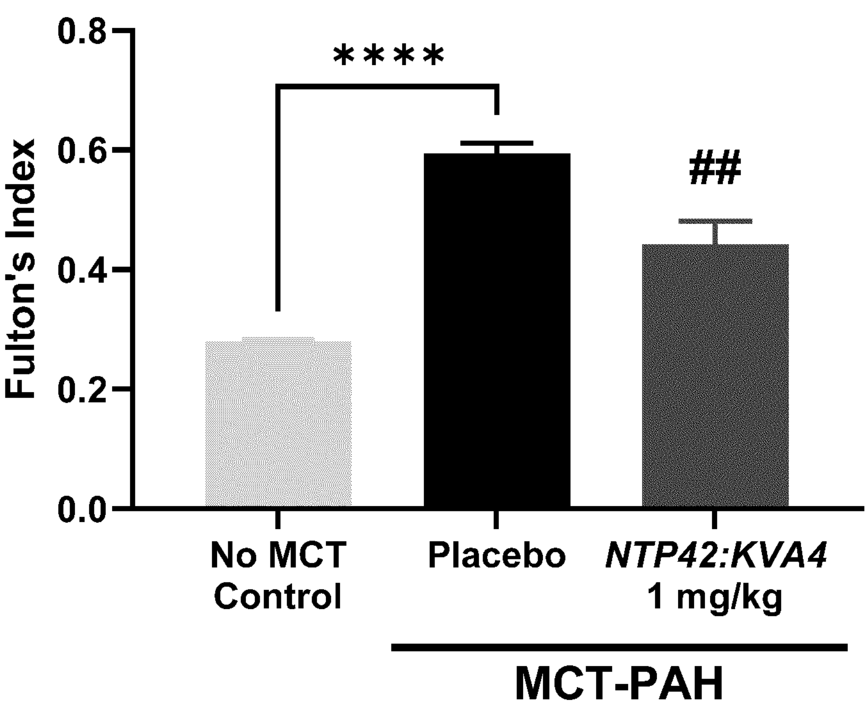
FIG. 22 gives results showing Cardiac Hypertrophy (Fulton's Index).
Figure 23:
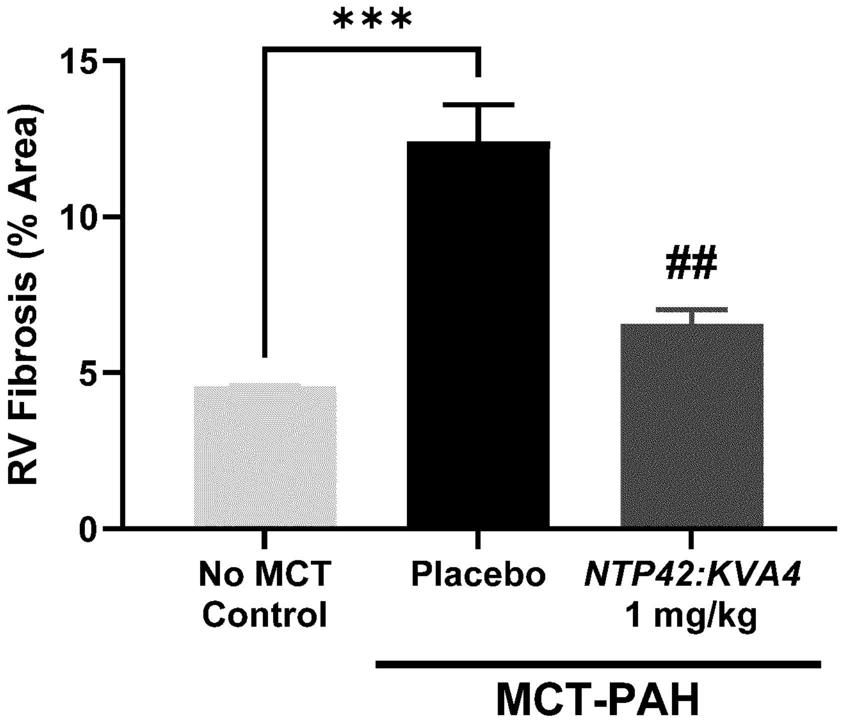
FIG. 23 gives results showing Right Ventricular Fibrosis.

Within the heart, NTP42:KVA4 reduced RV hypertrophy as assayed using the Fulton's Index and histological assessments of RV fibrosis demonstrated a significant treatment benefit for NTP42:KVA4 (FIG. 22 and FIG. 23).

Figure 24:
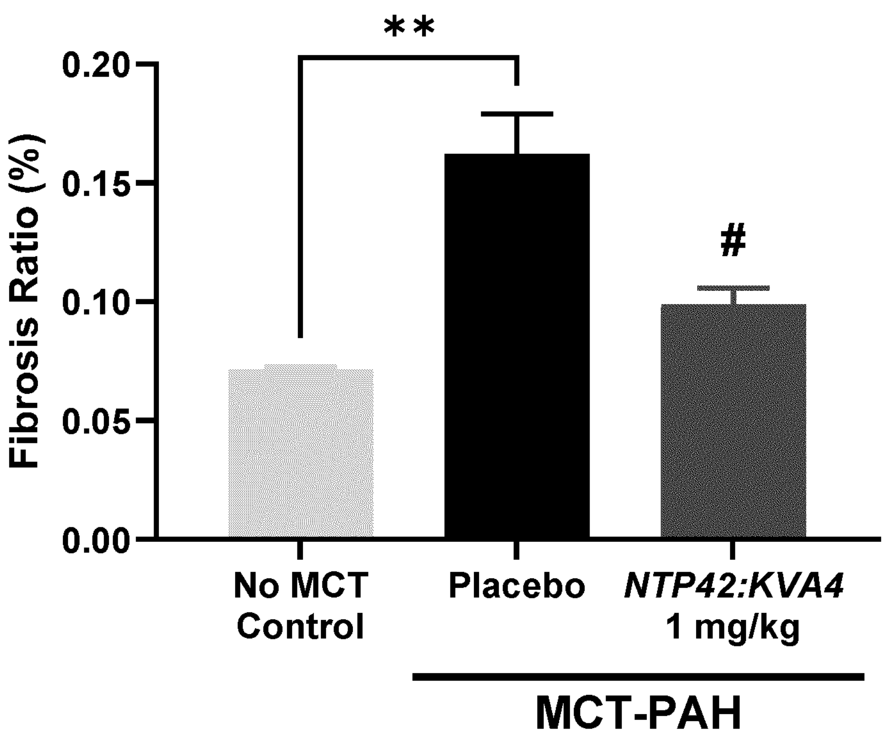
FIG. 24 gives results showing Pulmonary Fibrosis.
Figure 25:
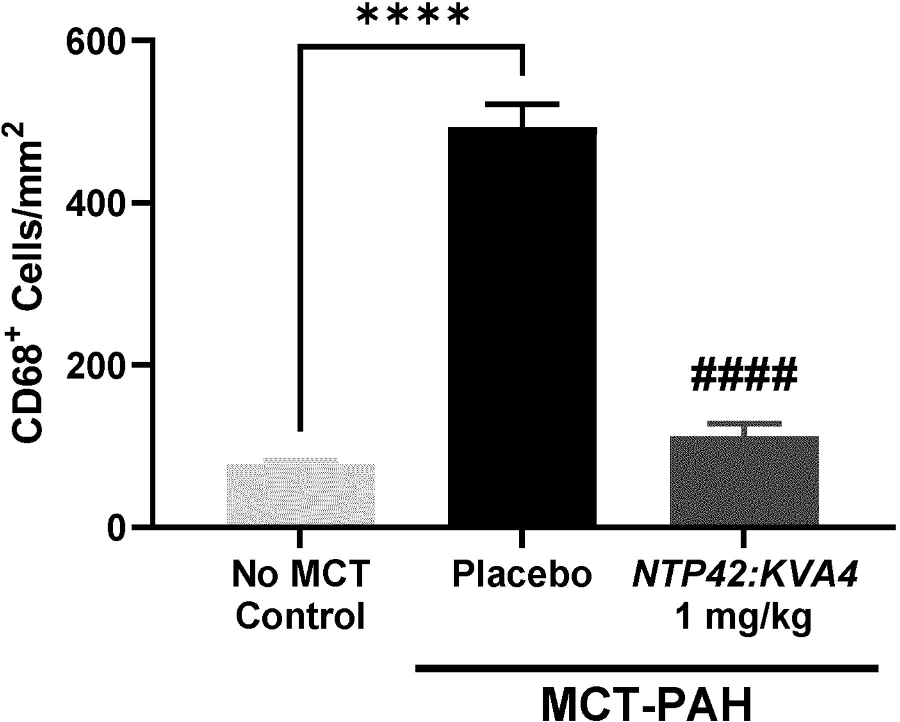
FIG. 25 gives results showing Lung Inflammation (CD68+ Macrophages).

In additional quantitative histological analyses, NTP42:KVA4 was shown to significantly reduce the extent of fibrosis surrounding small pulmonary arterioles as well as reducing the MCT-induced increase in CD68+ macrophage infiltration (FIG. 24 and FIG. 25).

FIG. 16-FIG. 25 show the effect of NTP42:KVA4 on Monocrotaline-Induced Pulmonary Arterial Hypertension in Rats. Male Sprague-Dawley rats were either injected subcutaneously with a single dose of monocrotaline (MCT; 60 mg/kg), or as control saline (No MCT). From Day 7 post-MCT injection animals were treated twice daily for 22 days with either NTP42:KVA4 (1 mg/kg), or as negative control, the placebo (30 mg/kg BID KOLLIDON VA 64) where all treatments were administered by oral gavage as a suspension in 0.5% (w/v) hydroxypropyl methylcellulose (HPMC). At Day 29, post-MCT induction, rats were anaesthetized for cardiac surgery and haemodynamic parameters recorded. Thereafter, the heart and lungs were removed en bloc, the wet weights of heart and lungs recorded and then fixed and processed for histopathology. Data presented within this figure include'

Figure 18:
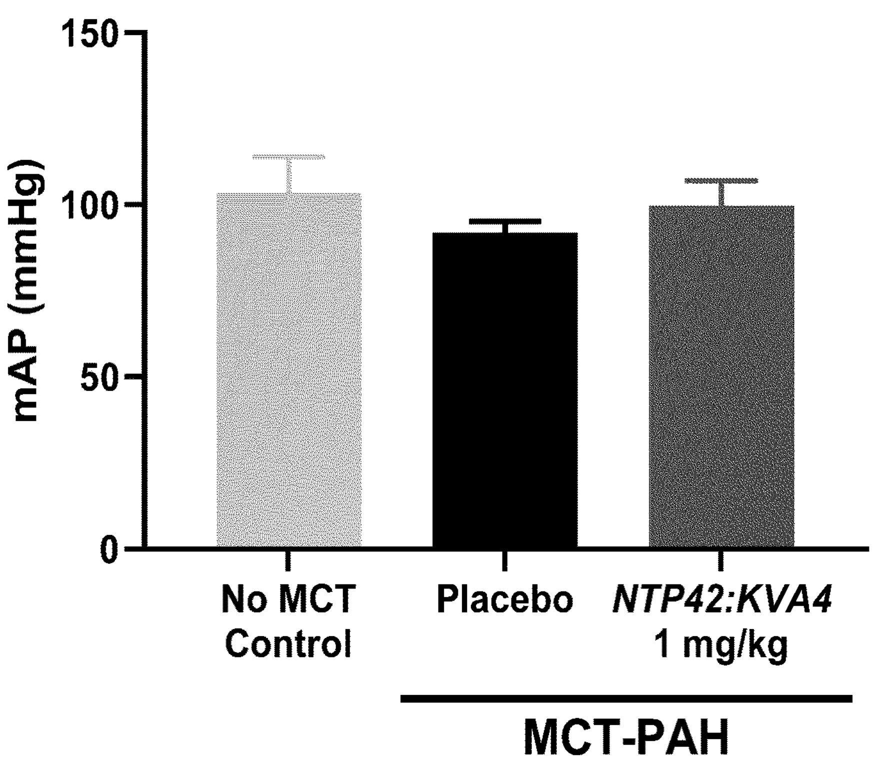
FIG. 18 gives results showing Systemic Arterial Pressure.

FIG. 16 shows mean pulmonary arterial pressure (mPAP);

FIG. 17 shows the right ventricular systolic pressure (RVSP);

FIG. 18 shows the mean systemic arterial pressure (mAP).

Figure 19:
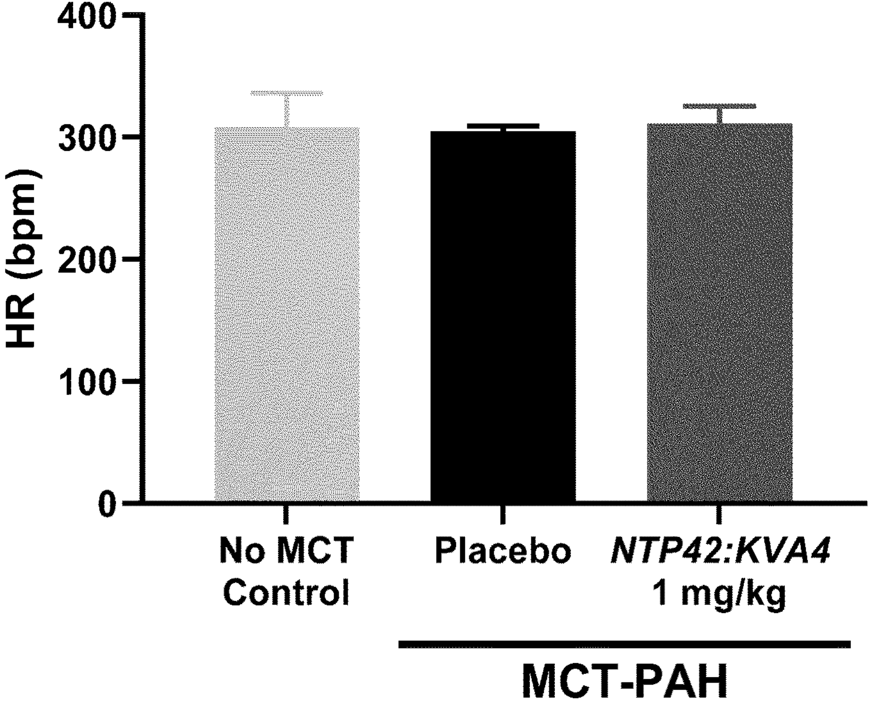
FIG. 19 gives results showing Heart Rate.

FIG. 19 shows heart rate (HR).

Figure 20:
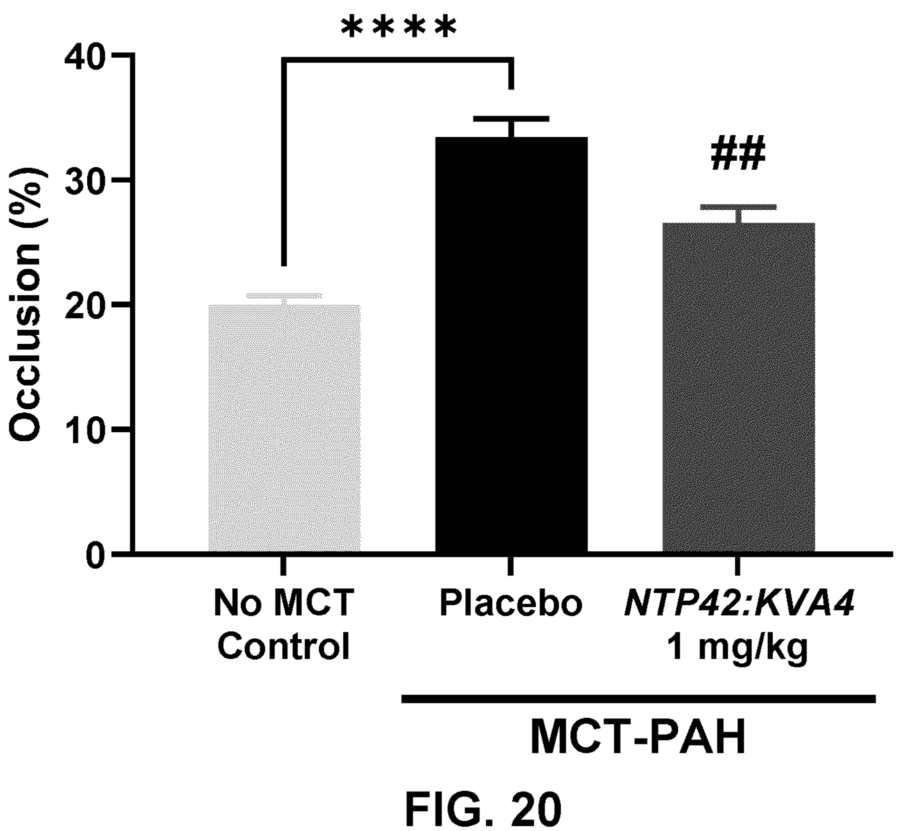
FIG. 20 shows Pulmonary Vascular Remodeling (Vessel Occlusion).
Figure 21:
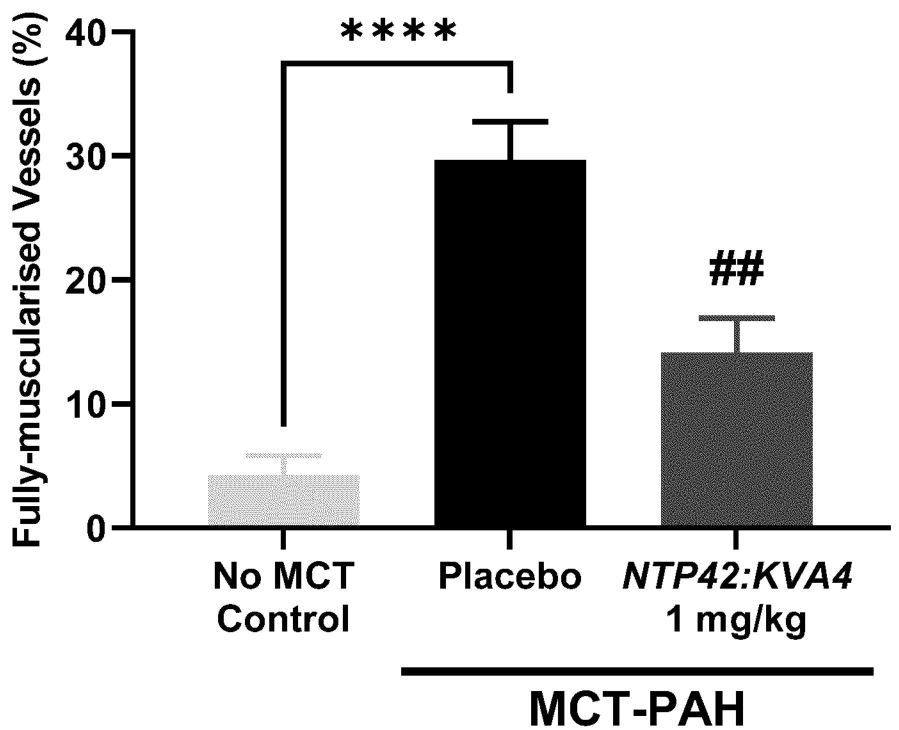
FIG. 21 shows Pulmonary Vascular Remodeling (Muscularised Vessels).

FIG. 20 shows pulmonary vascular remodeling, as vessel occlusion measured from morphometric assessments on haematoxylin and eosin (H&E)-stained sections.

FIG. 21 shows pulmonary vascular remodeling, as measured from assessments of the extent of muscularisation on anti-α-SMA-stained sections.

FIG. 22 shows the Fulton's Index of RV hypertrophy.

FIG. 23 shows cardiac (RV) fibrosis.

FIG. 24 shows the extent of pulmonary inflammation from analysis of CD68+ macrophage density.

FIG. 25 shows pulmonary fibrosis. For all of FIGS. 16-25, the mean (±S.E.M.) data is presented where asterisks indicate significant differences from the No MCT Control group and hashes indicate that the value is significantly different from the MCT Only Placebo group, and where */#, /##, */### and ****/#### correspond to $p<0.05$, $p<0.01$, $p<0.001$ and $p<0.0001$, respectively.

FIG. 26 is a table showing the effect of NTP42:KVA4 on Monocrotaline-Induced Pulmonary Arterial Hypertension in Rats.

Abbreviations: BID, bis in die/twice daily; bpm, beats per minute; CD68, cluster of differentiation 68; HR, heart rate; mAP, mean systemic arterial pressure; MCT, monocrotaline; mPAP, mean pulmonary arterial pressure; RVSP, right ventricular systolic pressure; SMA, α-smooth muscle actin.

FIG. 27 presents lung tissue sections showing the Effect of NTP42:KVA4 on the pulmonary vascular remodelling in the MCT-induced PAH rat model.

Formalin-fixed, paraffin-embedded (FFPE) lung tissue sections were stained with H&E and anti-α-smooth muscle actin & digitally scanned using the Aperio system. The representative images depict the extent of pulmonary vascular remodeling (H&E, left panels) and degree of muscularization (anti-α-SMA, right panels) of small pulmonary arterioles (10-50 μm) within the left lung. Morphometric assessments of H&E-stained slides and assessments of the extent of muscularization on anti-α-SMA-stained sections confirmed NTP42:KVA4 significantly reduced MCT-induced vascular remodeling. By way of example, the MCT-induced increase in percentage vessel occlusion was significantly reduced in animals treated with NTP42:KVA4 (1 mg/kg, BID; p=0.0019). The horizontal scale bar in each image corresponds to 20 μm, where all images were captured at 40× magnification.

Example 7: Demonstration of the In Vivo Efficacy of NTP42:KVA4 to Inhibit Aggregation of Platelets Ex Vivo in the Non-Human Primate (NHP) Cynomolgus Monkey The ability of NTP42 to inhibit platelet aggregation induced by thromboxane (TX) $A_2$ or its receptor, the TP, following the oral administration of the formulated drug product, NTP42:KVA4, has been demonstrated in the non-human primate (NHP) cynomolgus monkey. Whole blood platelet aggregation assays were performed ex vivo in blood samples taken from the NHPs (n=3) administered 100 mg/kg NTP42:KVA4, BID (200 mg/kg/day) for 14 days. In this type of platelet aggregation assay, a reduction in platelet numbers is indicative of platelet aggregation. Blood was collected prior to (pre-dose), and at 45 min- and 24 h-following the first daily dose, and platelet numbers determined in blood samples at baseline (untreated), and in blood samples incubated with drug vehicle, the thromboxane mimetic, U46619 or, as control, other platelet agonists (e.g., ADP, collagen, thrombin, ristocetin, epinephrine). Baseline platelet counts ranged from 120-190×103 platelets/μl.

Figure 28:
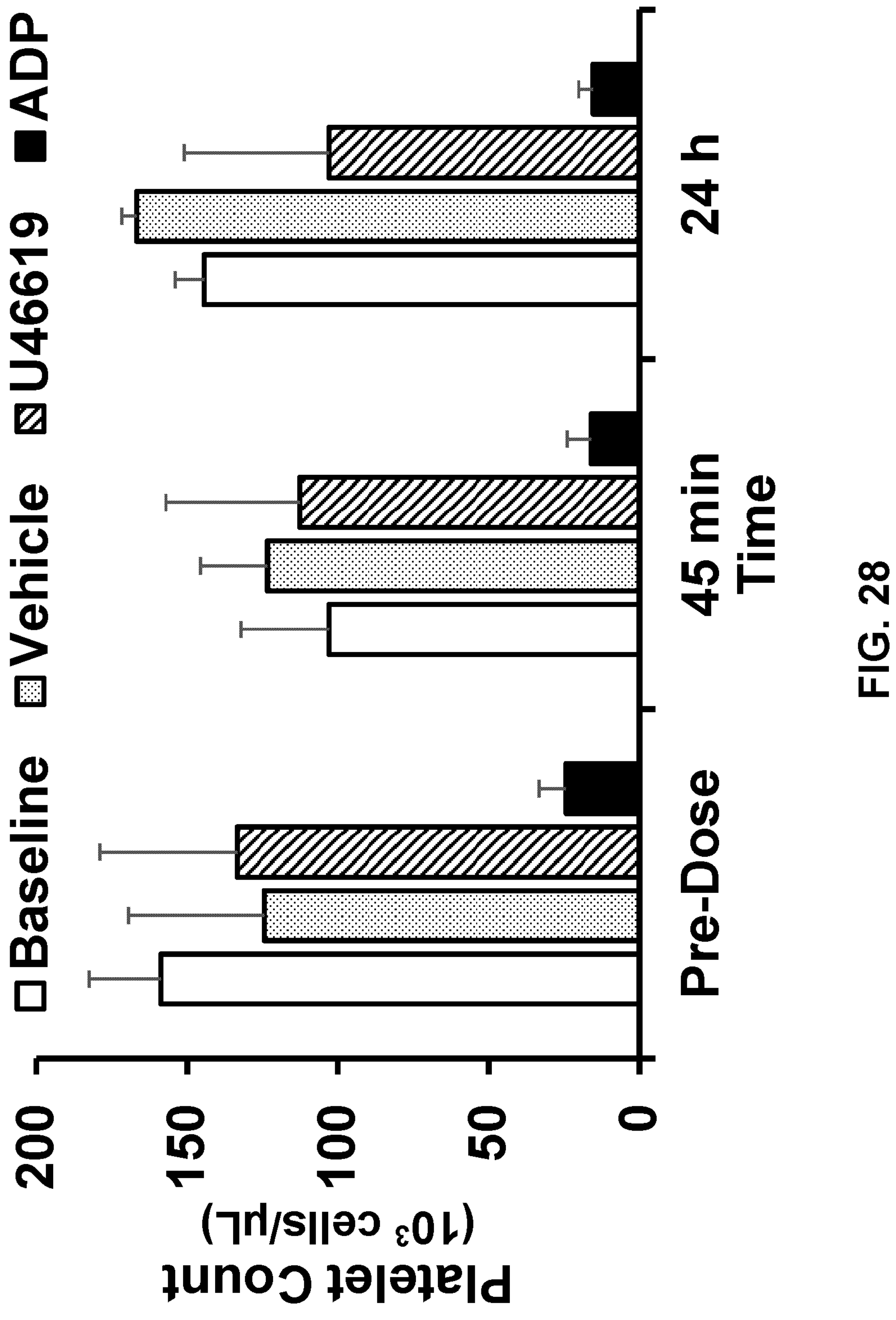
FIG. 28 shows results from whole blood platelet aggregation assays.

As shown in FIG. 28, administration of the formulated drug product NTP42:KVA4 inhibits $TXA_2$ (U46619)-induced platelet aggregation ex vivo (as measured by a decrease in platelet count) on Day 14 post-dosing but has no effect on aggregation induced by other platelet agonists in bloods from those same animals.

FIG. 28 shows whole blood platelet aggregation assays on Day 14 following twice daily oral dosing with 100 mg/kg/dose NTP42:KVA4 in the NHP cynomolgus monkey. Whole blood platelet aggregation assays were performed ex vivo in blood samples taken from the NHPs (n=3) administered 100 mg/kg NTP42:KVA4, BID (200 mg/kg/day) for 14 days. Blood was collected prior to (pre-dose), and at 45 min- and 24 h-following the first daily dose, and platelet numbers determined in blood samples at baseline (untreated), and in blood samples incubated with drug vehicle, the thromboxane mimetic, U46619 or, as control, 50 μM ADP. In this assay, a reduction in platelet numbers is indicative of platelet aggregation.

Specifically, following vehicle treatment, the platelet counts were similar to baseline values indicative that no aggregation occurred in response to the drug vehicle, as expected. There was also no reduction in platelet numbers at any time point in response to incubation of the blood samples with 1 μM U46619, even at pre-dosing on Day 14 of treatment. Supporting pharmacokinetic data confirmed NTP42 was present in the NHP plasma prior to the first daily dose and at levels sufficient to inhibit U46619-mediated aggregation of platelets. In contrast, platelet numbers were significantly reduced in response to incubation with other platelet agonists. By way of example, as shown in FIG. 28, platelet numbers were significantly reduced in response to 50 μM ADP, indicating that platelet aggregation had occurred in response to this agonist. Following 14-days of repeat dosing at 200 mg/kg/day, NTP42 levels in NHP plasma corresponded to Cmax values of 13,200 ng/ml, equivalent to 25 μM and, were still detectable 24 h post-dosing. Hence, as expected the drug, NTP42, selectively inhibited TP-mediated platelet aggregation but did not affect aggregation induced by other platelet agonists, e.g., 50 μM ADP. Critically, the study concluded "The lack of U46619-induced platelet aggregation suggests that NTP42 inhibited TP-mediated platelet aggregation and can be viewed as a pharmacodynamic indicator of TP receptor target engagement".

Example 8: Formulations for Use in Treatments

The results presented here show that formulations of the disclosure show significant cardiovascular and pulmonary benefits and may be used for amelioration of detrimental effects of various cardiopulmonary disorders.

Accordingly, embodiments of this disclosure provide any of the formulations of the disclosure for use in the treatment of a cardiopulmonary condition. The results present evidence for a reduction in pulmonary and cardiac fibrosis following NTP42/NTP42:KVA4 treatment with benefits in treating a pulmonary condition or a cardiac condition.

Some embodiments provide a formulation of the disclosure for use in the treatment of a pulmonary condition. Exemplary pulmonary conditions include; Idiopathic Pulmonary Fibrosis (IPF); Sarcoidosis; Autoimmune & Connective Tissue Diseases, e.g., Lupus, Scleroderma, Polymyositis & Dermatomyositis, Rheumatoid Arthritis; Exposure/Occupational Interstitial Lung Diseases, e.g., Asbestosis, Silicosis, Hypersensitivity Pneumonitis; and Treatment-related Interstitial Lung Disease following e.g., chemotherapy, radiation therapy, or certain medications.

Certain embodiments provide a formulation of the disclosure for use in the treatment of a cardiac condition. Exemplary cardiac conditions include; Hypertensive Heart Conditions, e.g., other PH groups besides PAH, but also left heart conditions including heart failure with preserved ejection fraction (HFpEF), heart failure with reduced ejection fraction (HFrEF), etc.; Muscular Dystrophy (MD) where cardiomyopathy is implicated, e.g. Duchenne Muscular Dystrophy (DMD), Limb-girdle Muscular Dystrophy (LGMD), Becker Muscular Dystrophy (BMD); Idiopathic Dilated Cardiomyopathy (DCM); Diabetic Cardiomyopathy; and Scarring following Myocardial Infarction (MI).

Accordingly, embodiments of this disclosure provide any of the formulations of the disclosure for use in a method of treating a pulmonary condition. The pulmonary condition may be selected from the group consisting of: bronchial asthma, chronic obstructive pulmonary disorder, COVID-19 related pulmonary hypertension, COVID-19 related pulmonary microvessel thrombosis, COVID-19 related pulmonary fibrosis, pulmonary inflammation, dermatomyositis, idiopathic pulmonary fibrosis, Exposure/Occupational interstitial lung diseases, Treatment-related interstitial lung diseases, polymyositis, pulmonary arterial hypertension, pulmonary fibrosis, pulmonary hypertensions, rheumatoid arthritis, sarcoidosis, scleroderma, and systemic lupus erythematosus.

Also, embodiments of this disclosure provide any of the formulations of the disclosure for use in a method of treating a cardiovascular condition. The cardiovascular condition may be selected from the group consisting of: heart failure, muscular dystrophy, idiopathic dilated cardiomyopathy, diabetic cardiomyopathy, atherothrombosis, stroke, myocardial infarction, atherosclerosis, arteriosclerotic vascular disease, thromboembolism, deep vein thrombosis, arterial thrombosis, COVID-19 related cardiac microvessel thrombosis, COVID-19 related systemic microvessel thrombosis, ischemia, peripheral vascular disease, peripheral artery occlusive disease, coronary artery disease, angina pectoris, and transient ischemic attack.

DISCUSSION

The formulations present a high-quality drug product that is suitable for First-in-Human Phase I Clinical Trials to evaluate the safety and tolerability of the formulation in a clinical setting.

Using an Amorphous Solid Dispersion approach, a Spray-Dried Dispersion formulation with the pharmaceutically acceptable vinylpyrrolidone-vinyl acetate copolymer with an NTP42: polymer ratio of 1:4, referred to as NTP42:KVA4 (wherein the vinylpyrrolidone-vinyl acetate copolymer is abbreviated to KVA and 4 indicates the drug:polymer ratio) has been found to have improved bioavailability compared to NTP42 alone. NTP42:KVA4 has demonstrated enhanced dissolution compared to the active pharmaceutical ingredient alone in the biorelevant media, e.g., Fasted State Simulated Intestinal Fluid (FaSSIF; pH 6.5) as illustrated in FIG. 1

The invention describes formulations that offer enhanced solubility and excellent exposure and oral bioavailability compared to the active pharmaceutical ingredient NTP42 alone. Moreover, a candidate drug product, NTP42:KVA4 has been found to have advantageous properties over formulations comprising different polymers and different ratios of active pharmaceutical ingredient to polymer. The drug may be administered orally as a "Drug-in-Bottle" format, with NTP42:KVA4 administered in a suitable dosing vehicle, e.g., 0.5% hydroxypropyl methylcellulose E3.

A surprising advantage of the spray solid dispersion formulation is that the vinylpyrrolidone-vinyl acetate copolymer confers a protective effect on benzenesulfonyl urea, protecting it from low pH e.g., FaSSGF, pH 1.6 maintaining it in complex for release at higher pH, e.g., FaSSIF, pH 6.5. Hence, based on the dissolution data, benzenesulfonyl urea in complex with vinylpyrrolidone-vinyl acetate in a spray solid dispersion material would be protected from the acidic environment of the stomach, pH 1.6 and disperse in the higher pH environment of the intestine where it may be maximally absorbed. By the present invention the pH dependent solubility and release of benzenesulfonyl urea in formulations comprising benzenesulfonyl urea and vinylpyrrolidone-vinyl acetate copolymer was discovered.

Surprisingly, lowering the drug-loading, such as in the case of benzenesulfonyl urea in complex with vinylpyrrolidone-vinyl acetate at 1:8 ratio (benzenesulfonyl urea:vinylpyrrolidone-vinyl acetate), did not lead to enhanced dissolution in low pH (e.g. in FaSSGF, pH 1.6). Moreover, raising the drug loading, such as in the case of benzenesulfonyl urea in complex with vinylpyrrolidone-vinyl acetate at 1:1 ratio (benzenesulfonyl urea:vinylpyrrolidone-vinyl acetate), did not alter the release of benzenesulfonyl urea or enhance its dissolution on switching from low pH (e.g. in FaSSGF, 1.6) to higher pH (e.g., in FaSSIF, pH 6.5).

In contrast, formulations of non-steroidal anti-inflammatory drugs and non-steroidal anti-inflammatory drugs in polymer complexes display dissolution rates dependent on drug loading. For example, non-steroidal anti-inflammatory drugs with lower drug-loading often dissolve in their entirety in lower pH environments, regardless of the complexes in which they are formulated. Therefore, the dissolution properties of the formulations of the invention are unique and are entirely distinct from those observed in the case of other drug and drug:polymer formulations.

Moreover, many drugs, for example non-steroidal anti-inflammatory drugs, are preferably formulated from compress/compacted material and hot melt extrusion manufacturing processes. In contrast, benzenesulfonyl urea: vinylpyrrolidone-vinyl acetate formulations of the present invention were surprisingly found to have improved dissolution and bioavailability when formulated as amorphous solid dispersions, for example spray dried dispersions. This process, in contrast to hot melt extrusions, allows the complexes to be formed at controlled temperatures that preserve the internal chemistry to the benzenesulfonyl ureas in order to effectively act as antagonists for the T prostanoid receptor when maximally released in the intestine.

The various described embodiments of the invention may be used in conjunction with one or more other embodiments unless technically incompatible.

The invention claimed is:

1. A formulation comprising:

a spray dried amorphous solid dispersion comprising:

a drug comprising a substituted benzenesulfonyl urea of formula (IV)

(IV)

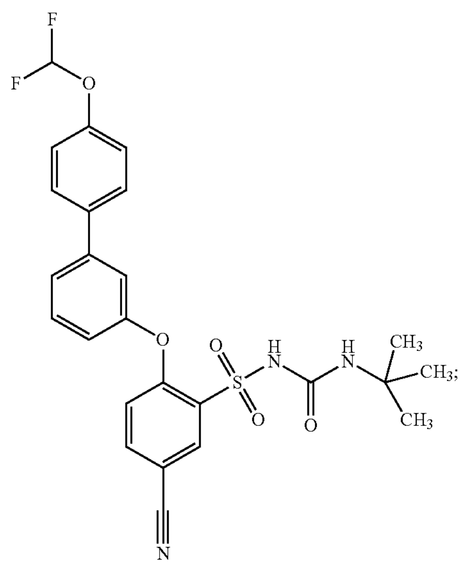

a vinylpyrrolidone-vinyl acetate copolymer, wherein a ratio of the substituted benzenesulfonyl urea to the vinylpyrrolidone-vinyl acetate copolymer is between 1:4 and 1:8.

2. The formulation of claim 1, formulated in an oral dose form.

3. The formulation of claim 1, wherein there is less dissolution of the formulation in environments with a pH less than 2 than in environments with a pH above 5.

4. The formulation of claim 1, wherein there is no dissolution of the formulation at a pH of less than 2.

5. The formulation of claim 4, wherein there is substantial dissolution of the formulation at a pH above 5.

6. The formulation of claim 1, wherein a ratio of the substituted benzenesulfonyl urea to the vinylpyrrolidone-vinyl acetate copolymer is 1:4.

7. The formulation of claim 1, wherein the ratio is about 1:4; wherein there is no dissolution of the formulation at a pH of less than 2; and wherein there is substantial dissolution of the formation at a pH above 5.

8. The formulation of claim 7, formulated in an oral dose form.

9. A method of treating a cardiopulmonary condition, the method comprising administering to a patient a formulation of claim 8, wherein the cardiopulmonary condition is pulmonary arterial hypertension.

* * * * *